(12) United States Patent
Ades et al.

(10) Patent No.: US 7,919,104 B2
(45) Date of Patent: Apr. 5, 2011

(54) FUNCTIONAL EPITOPES OF STREPTOCOCCUS PNEUMONIAE PSAA ANTIGEN AND USES THEREOF

(75) Inventors: Edwin W. Ades, Atlanta, GA (US); Jacquelyn S. Sampson, College Park, GA (US); Sandra Steiner, Atlanta, GA (US); George M. Carlone, Stone Mountain, GA (US); Joseph J. Caba, Atlanta, GA (US); GowriSankar Rajam, Tucker, GA (US)

(73) Assignee: The United States of America as represented by the Department of Health and Human Services, Centers for Disease Control and Prevention, Washington, DC (US)

( * ) Notice: Subject to any disclaimer, the term of this patent is extended or adjusted under 35 U.S.C. 154(b) by 143 days.

(21) Appl. No.: 11/992,719

(22) PCT Filed: Jul. 29, 2005

(86) PCT No.: PCT/US2005/027290
§ 371 (c)(1),
(2), (4) Date: Jul. 18, 2008

(87) PCT Pub. No.: WO2006/127020
PCT Pub. Date: Nov. 30, 2006

(65) Prior Publication Data
US 2008/0305123 A1 Dec. 11, 2008

Related U.S. Application Data

(60) Provisional application No. 60/682,495, filed on May 19, 2005.

(51) Int. Cl.
*A61K 39/09* (2006.01)
*A61K 39/02* (2006.01)
*A61K 39/38* (2006.01)
*A61K 38/00* (2006.01)
*A01N 37/18* (2006.01)

(52) U.S. Cl. ............... 424/244.1; 424/242.1; 424/234.1; 424/190.1; 424/193.1; 424/184.1; 514/2; 530/300; 530/825

(58) Field of Classification Search ........................ None
See application file for complete search history.

(56) References Cited

FOREIGN PATENT DOCUMENTS
WO    WO 02/04497 A2    1/2002
WO    WO 05/003174 A1   1/2005

OTHER PUBLICATIONS

Abbas et al. Cellular and Molecular Immunology 2000 Chapter 15 p. 360-362.*
Ellis, R.W. (Chapter 29 of "Vaccines" [Plotkin, S.A. et al. (eds) published by W. B. Saunders company (Philadelphia), 1988.*
Poolman et al (Expert Rev. Vaccines 3 (5), 597-604 (2004).*
Romero-Steiner. Clinical and Diagnostic Laboratory Immunology, Mar. 2003, p. 246-251.*
Weiser et al. Infection and Immunity, Jun. 1996, p. 2240-2245 a.*
Anderson et al. Infection and Immunity, Apr. 1981, p. 311-317.*
Johnson et al., "Inhibition of Pneumococcal Carriage in Mice by Subcutaneous Immunization with Peptides from the Common Surface Protein Pneumococcal Surface Adhesin A," *The Journal of Infectious Diseases*, 185(4):489-496 (2002).
Morrison et al., "Confirmation of *psaA* in All 90 Serotypes of *Streptococcus pneumonia* by PCR and Potential of This Assay for Identification and Diagnosis," *Journal of Clinical Microbiology*, 38(1):434-437 (2000).
Schmeck et al., "*Streptococcus pneumoniae*-induced p38 MAPK-dependent Phosphorylation of RelA at the Interleukin-8 Promotor," *The Journal of Biological Chemistry*, 279(51):53241-53247 (2004).
Srivastava et al., "Selection of an Immunogenic and Protective Epitope of the PsaA Protein of *Streptococcus pneumoniae* Using a Phage Display Library," *Hybridoma*, 19(1):23-31 (2000).

* cited by examiner

*Primary Examiner* — N. M. Minnifield
*Assistant Examiner* — Oluwatosin Ogunbiyi
(74) *Attorney, Agent, or Firm* — Klarquist Sparkman, LLP

(57) ABSTRACT

Provided is a P4 peptide, which contains functional epitopes of the PsaA protein of *Streptococcus pneumoniae*, and related methods and compositions. P4 peptide mimetics having a conformational structure identical or similar to the conformation of P4 (e.g., SEQ ID NO: 1 and SEQ ID NO:2) are provided. An antibody that specifically binds to the epitope defined by the disclosed peptides is provided. A P4-specific antibody is PsaA-specific since P4 defines an epitope specific for PsaA. Immunogenic compositions comprising the peptide of SEQ ID NO: 1 and a pharmaceutical carrier or the peptide of SEQ ID NO:2 and a pharmaceutical carrier are also provided. Methods of using the peptides and antibodies of the invention are provided.

6 Claims, 8 Drawing Sheets

Figure 3.
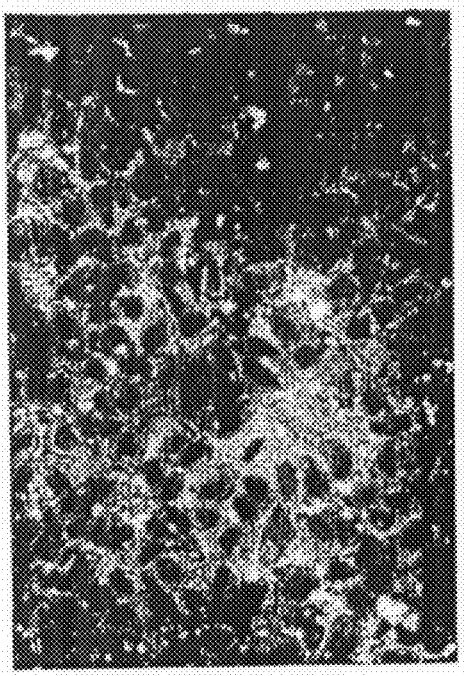
A
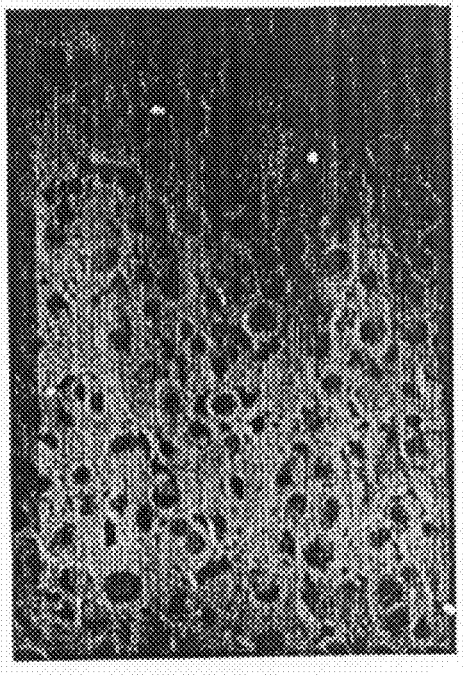
B

FIG 4

```
         strand 7              α-helix 8                    strand 8
248
VPS LFVES SVDD RPMKTVSQDT NI PIYAQI FT              PsaA (SEQ ID No: 2, AA1-32)
               KYS RVPWTAWAPHG X                    P1 (SEQ ID No: 3)
               RLYQHDLRA X GFWRL                    P2 (SEQ ID No: 4)
     I NRRF W HR R W HVE-RQ                         P3 (SEQ ID No: 5)
    LFVES SVKRI RPMKTVSQDT NI PIYAQI F              P4 (SEQ ID No: 1)

309
                 α-helix 9
DSIAEQGKEGDR YYSMMKYNLDKIAEGL AK  COO⁻ PsaA (SEQ ID No: 18)
```

FUNCTIONAL EPITOPES OF *STREPTOCOCCUS PNEUMONIAE* PSAA ANTIGEN AND USES THEREOF

CROSS REFERENCE TO RELATED APPLICATIONS

This is the §371 U.S. National Stage of International Application No. PCT/US2005/027290, filed Jul. 29, 2005, which was published in English under PCT Article 21(2), which in turn claims the benefit of U.S. Provisional Application No. 60/682,495, filed May 19, 2005, which is incorporated by reference herein in its entirety.

BACKGROUND

*Streptococcus pneumoniae* is a leading cause of global morbidity and mortality, resulting in 1.5 million deaths every year worldwide, for example, from pneumonia, bacteremia, meningitis, and otitis media primarily in children <5 years old.

Successful polysaccharide vaccines are available in the United States. However, countries with limited resources cannot afford these vaccines. The current vaccines (23-valent polysaccharide (adults); and 7-valent polysaccharide (children)) protect against more prevalent serotypes. There are 90 known serotypes of *Streptococcus pneumoniae*. However there is a need for a vaccine that protects against all known serotypes. Pneumococcal surface adhesin A (PsaA) is a streptococcal common protein, and is a vaccine candidate which could be affordable for all countries.

SUMMARY

Provided is a P4 peptide, which contains an epitope of the PsaA protein of *Streptococcus pneumoniae*, and related methods and compositions.

BRIEF DESCRIPTION OF THE FIGURES

FIG. 3 shows adherence of rPsaA-coated fluorospheres to Detroit 562 nasopharyngeal cells. Panel A. rPsaA-coated fluospheres (Molecular Probes, 1 µm in diameter) adherent after 5 washes per well. Panel B. Inhibition of adherence of rPsaA-coated fluospheres by addition of human serum (serum 7074, 1:10 dilution) containing anti-PsaA antibodies (18.3 µg/ml, undiluted). Field magnification 400×. Images were captured using a Leitz inverted fluorescent microscope and a digital camera. Fluosphere diameter is 1 µm.

FIG. 4 shows the identification of peptide 4 (P4) amino acid sequence by comparison of peptides P1, P2, and P3 sequences to the PsaA region in question.

DETAILED DESCRIPTION

Figure 1:
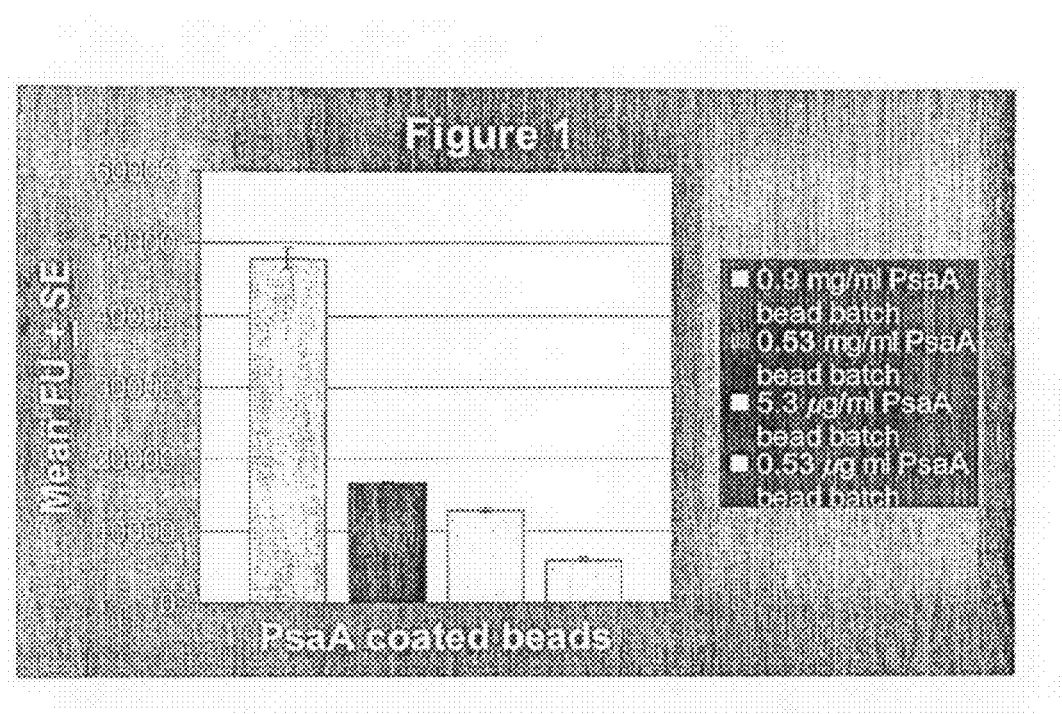
FIG. 1 shows mean adherence of 0.9 mg/ml, 0.53 mg/ml, 5.3 µg/ml, and 0.53 µg/ml rPsaA-coated beads to Detroit 562 cells (mean FU±SE) when 1,640±210 beads were added per well.
Figure 2:
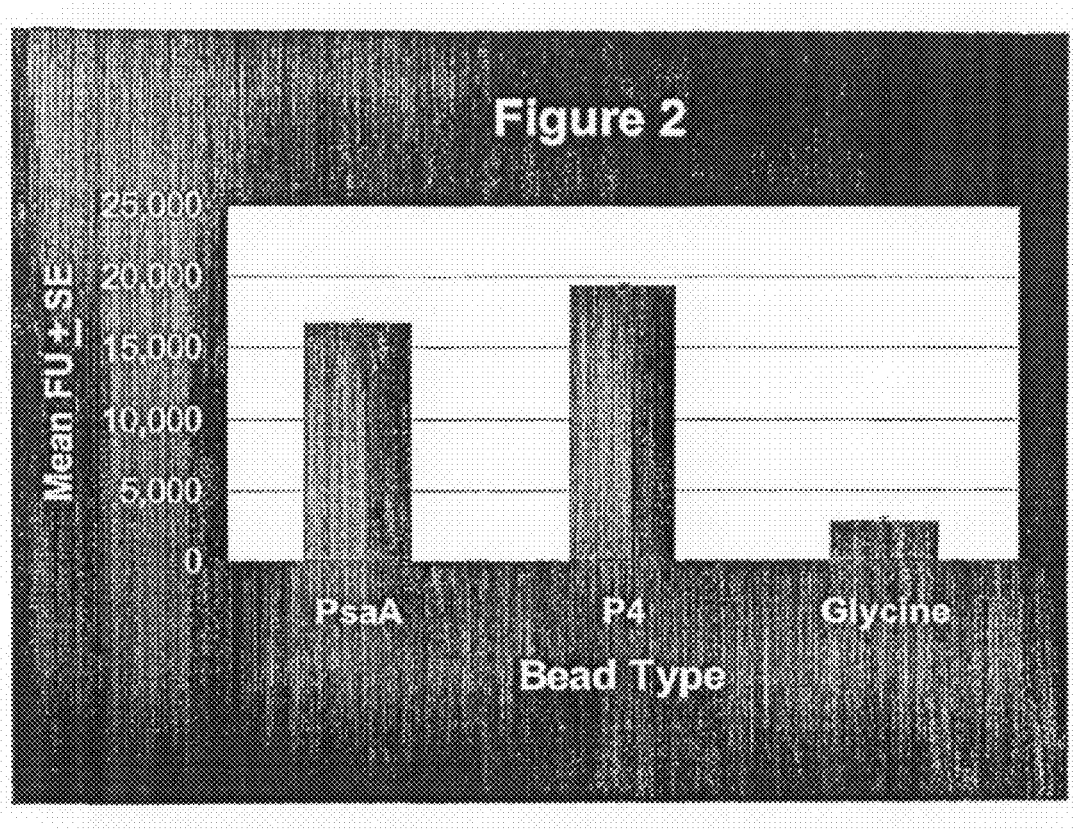
FIG. 2 shows adherence of the 0.53 mg/ml batch of PsaA beads, P4-coated beads, and Glycine-coated control beads when 1640±210 beads were added per well.

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

The Sequence Listing is submitted as an ASCII text file in the form of the file named Sequence_Listing.txt, which was created on May 18, 2010, and is 7,810 bytes, which is incorporated by reference herein.

Peptides/Polypeptides/Proteins

Provided is a P4 peptide, which contains an epitope of the PsaA protein of *Streptococcus pneumoniae*. A peptide that comprises the amino acid sequence defined in SEQ ID NO:1 (LFVESSVKRRPMKTVSQDTNIPIYAQIF), an example of the P4 peptide, is provided.

Also provided is a peptide comprising the amino acid sequence defined as LFVDSSV DDRPMKTVSQDTNIPIYAQIF (SEQ ID NO:2). This peptide is a further example of a P4 peptide, and differs from SEQ ID NO:1 in that the D at residue 4 is E in P4, and the two underlined amino acids (DD at positions 8 and 9) are "KR" in the P4 sequence. A P4 peptide of the invention can have one, two or all three of the amino acid substitutions shown in SEQ ID NO:2.

The term "peptide" or "peptide portion" is used broadly herein to mean two or more amino acids linked by a peptide bond. The term "fragment" or "proteolytic fragment" is used herein to refer to a product that can be produced by a proteolytic reaction on a polypeptide, i.e., a peptide produced upon cleavage of a peptide bond in the polypeptide. Although the term "proteolytic fragment" is used generally herein to refer to a peptide that can be produced by a proteolytic reaction, it should be recognized that the fragment need not necessarily be produced by a proteolytic reaction, but also can be produced using methods of chemical synthesis or methods of recombinant DNA technology, to produce a synthetic peptide that is equivalent to a proteolytic fragment. It should be recognized that the term "peptide" is not used herein to suggest a particular size or number of amino acids comprising the molecule, and that a peptide of the invention can contain up to several amino acid residues or more.

By "isolated polypeptide" or "purified polypeptide" is meant a polypeptide (or a fragment thereof) that is substantially free from the materials with which the polypeptide is normally associated in nature. The polypeptides of the invention, or fragments thereof, can be obtained, for example, by extraction from a natural source (e.g., a bacterial cell), by expression of a recombinant nucleic acid encoding the polypeptide (e.g., in a cell or in a cell-free translation system), or by chemically synthesizing the polypeptide. In addition, polypeptide fragments may be obtained by any of these methods, or by cleaving full length PsaA protein followed by fragment purification.

A fragment of a reference protein or polypeptide includes only contiguous amino acids of the reference protein/polypeptide, and is at least one amino acid shorter than the reference sequence.

Variants of the SEQ ID NO:1 are also provided. For example, the peptide of SEQ ID NO:2 is a variant of the peptide of SEQ ID NO:1. Variants of the SEQ ID NO:2 are also provided.

The peptide can comprise amino acids in addition to those set forth in SEQ ID NO:1 and SEQ ID NO:2. For example, the additional amino acids can correspond to one or more contiguous N-terminal and/or C-terminal amino acids of PsaA. In one example the peptide consists of SEQ ID NO:1, plus combinations of from 0 to 6 amino acids on the N-terminus and from 0 to 6 amino acids on the C-terminus, wherein the amino acids are contiguous amino acids that flank SEQ ID NO: 1 in a native (also referred to as "wild type" or "naturally occurring") PsaA (for example, the PsaA disclosed in GenBank, NCBI, Blast database available on the World Wide Web at ncbi.nlm.nih.gov/blast/Blast.cgi, under accession number gi|7920462|gb|AAF70667.1). In most instances there are from 0 to 3 additional amino acids on each end, wherein the amino acids are contiguous amino acids that flank SEQ ID NO:1 in a native (also referred to as "wild type" or "naturally occurring") PsaA (for example, the PsaA disclosed in GenBank Accession no. gi|7920462|gb|AAF70667.1). Thus, the peptide can consist of SEQ ID NO:6. The longer peptide variant of P4 retains at least one function of P4.

In addition, other derivatives of the peptides which also function in the disclosed methods and compositions are contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. Typically, no more than about from 2 to 6 residues are deleted at any one site within the protein molecule. These variants ordinarily are prepared by site specific mutagenesis of nucleotides in the DNA encoding the protein, thereby producing DNA encoding the valiant, and thereafter expressing the DNA in recombinant cell culture. Techniques for making substitution mutations at predetermined sites in DNA having a known sequence are well known, for example M13 primer mutagenesis and PCR mutagenesis. Amino acid substitutions are typically of single residues, but can occur at a number of different locations at once; insertions usually will be on the order of about from 1 to 10 amino acid residues; and deletions will range about from 1 to 30 residues. Deletions or insertions preferably are made in adjacent pairs, i.e. a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure. Substitutional variants are those in which at least one residue has been removed and a different residue inserted in its place. Such substitutions generally are made in accordance with the following Tables 1 and 2 and are referred to as conservative substitutions.

TABLE 1

Amino Acid Abbreviations

| Amino Acid | Abbreviations |
|---|---|
| alanine | Ala; A |
| allosoleucine | AIle |
| arginine | Arg; R |
| asparagine | Asn; N |
| aspartic acid | Asp; D |
| cysteine | Cys; C |
| glutamic acid | Glu; E |
| glutamine | Gln; K |
| glycine | Gly; G |
| histidine | His; H |
| isolelucine | Ile; I |
| leucine | Leu; L |
| lysine | Lys; K |
| phenylalanine | Phe; F |
| proline | Pro; P |
| pyroglutamic acidp | Glu |
| serine | Ser; S |
| threonine | Thr; T |
| tyrosine | Tyr; Y |
| tryptophan | Trp; W |
| valine | Val; V |

TABLE 2

Amino Acid Substitutions

| Original Residue | Exemplary Substitutions |
|---|---|
| Arg | Lys, Gln |
| Asn | Gln |
| Asp | Glu |
| Cys | Ser |
| Gln | Asn |
| Glu | Asp |
| Gly | Pro |
| His | Gln |
| Ile | leu; val |
| Leu | ile; val |
| Lys | arg; gln |
| Met | leu; ile |
| Phe | met; leu; tyr |
| Ser | Thr |
| Thr | Ser |
| Trp | Tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g.

seryl or threonyl, is substituted for (or by) a hydrophobic residue, e.g. leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. For example, a conservative substitution would be replacing one hydrophobic residue for another, or one polar residue for another. Such conservatively substituted variations of each explicitly disclosed sequence are included within the mosaic polypeptides provided herein.

A conservative substitution is a substitution of an amino acid residue for another amino acid residue having similar biochemical properties. In a particular example, a conservative substitution is an amino acid substitution in a peptide that does not substantially affect the biological function of the peptide. A peptide can include one or more amino acid substitutions, for example 1-10 conservative substitutions, 2-5 conservative substitutions, 4-9 conservative substitutions, such as 2, 5 or 10 conservative substitutions. More specifically, a peptide of at least 20 amino acids can have 1-2 conservative substitutions, a peptide of at least about 25 amino acids can have 1-3 conservative substitutions, and a peptide of at least about 35 amino acids can have 1-4 conservative substitutions. In other words up to about 10% of the amino acids in a peptide can be conservatively substituted.

For example, a variant having a conservative substitution in the P4 peptide (such as a peptide having the sequence provided in SEQ ID NO:7-15) does not substantially affect the ability of the P4 peptide to 1) bind or attach to the PsaA receptor, 2) generate a PsaA-specific antibody when used as an immunogen, 3) inhibit or block binding or attachment of PsaA to its receptor, 4) induce eukaryotic cell activation resulting in reduction of a) cytokines such as IL-8, IL-6, EGF or b) cell surface membrane ruffling or nuclear changes, or an increase in cytokines such as FGFbasic or 6) increase phagocytic activity against *S. pneumoniae*. The nuclear changes can include becoming more granular and fragmented. The cytoplasm is vacuolated and has projections of pseudopodia as detected by TEM (transmission electron microscopy). Invasion or internalization of bacteria was demonstrated by survival to gentamycin treatment (45%) after adherence assays were performed.

As used herein, the phrase "specific" in the context of antibody binding refers to a binding reaction which is determinative of the presence of the P4 peptide and *S. pneumoniae* PsaA in a heterogeneous population of proteins, proteoglycans, and other biologics. Thus, under designated conditions, the antibodies or fragments thereof of the present invention bind to an epitope defined by the P4 peptide or a P4-specific mimetic or variant and do not bind in a significant amount to other proteins or proteoglycans present in the subject.

Herein, "inhibition" or "inhibits" means to reduce the specified activity, e.g., binding. Thus, it is understood that inhibition can mean a slight reduction in binding to the complete blocking of binding. An "inhibitor" can be anything that reduces the recited activity.

A polypeptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods. An alanine scan can be used to identify which amino acid residues in a protein can tolerate an amino acid substitution. In one example, the biological activity of the protein is not decreased by more than 25%, for example not more than 20%, for example not more than 10%, when an alanine, or other conservative amino acid (such as those listed below), is substituted for one or more native amino acids.

Examples of amino acids which can be substituted for an original amino acid in a protein and which are regarded as conservative substitutions include, but are not limited to: Ser or Gly for Ala; Lys for Arg; Gln or His for Asn; Glu for Asp; Ser for Cys; Asn for Gln; Asp for Glu; Pro for Gly; Asn or Gln for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Examples of functional P4 peptides with substitutions relative to SEQ ID NO:1 are provided in SEQ ID NOS: 7-15.

Further information about conservative substitutions can be found in, among other locations in, Ben-Bassat et al., (J. Bacteriol. 169:751-7, 1987), O'Regan et al., (Gene 77:237-51, 1989), Sahin-Toth et al., (Protein Sci. 3:240-7, 1994), Hochuli et al., (Bio/Technology 6:1321-5, 1988) and in standard textbooks of genetics and molecular biology.

It is understood that there are numerous amino acid and peptide analogs which can be incorporated into the disclosed compositions. For example, there are numerous D amino acids or amino acids which have a different functional substituent than the amino acids shown in Table 1 and Table 2. The opposite stereo isomers of naturally occurring peptides are disclosed, as well as the stereo isomers of peptide analogs. These amino acids can readily be incorporated into polypeptide chains by charging tRNA molecules with the amino acid of choice and engineering genetic constructs that utilize, for example, amber codons, to insert the analog amino acid into a peptide chain in a site specific way (Thorson et al., Methods in Molec. Biol. 77:43-73 (1991), Zoller, Current Opinion in Biotechnology, 3:348-354 (1992); Ibba, Biotechnology & Genetic Engineering Reviews 13:197-216 (1995), Cahill et al., TIBS, 14(10):400-403 (1989); Benner, TIB Tech, 12:158-163 (1994); Ibba and Hennecke, Bio/technology, 12:678-682 (1994) all of which are herein incorporated by reference at least for material related to amino acid analogs).

Molecules can be produced that resemble peptides, but which are not connected via a natural peptide linkage. For example, linkages for amino acids or amino acid analogs can include $CH_2NH$—, —$CH_2S$—, —$CH_2$—$CH_2$—, —CH═CH— (cis and trans), —$COCH_2$—, —CH(OH)$CH_2$—, and —$CHH_2SC$—(These and others can be found in Spatola, A. F. in Chemistry and Biochemistry of Amino Acids, Peptides, and Proteins, B. Weinstein, eds., Marcel Dekker, New York, p. 267 (1983); Spatola, A. F., Vega Data (March 1983), Vol. 1, Issue 3, Peptide Backbone Modifications (general review); Morley, Trends Pharm Sci (1980) pp. 463-468; Hudson, D. et al., Int J Pept Prot Res 14:177-185 (1979) (—$CH_2NH$—, $CH_2CH_2$—); Spatola et al. Life Sci 38:1243-1249 (1986) (—$CHH_2$—S); Hann J. Chem. Soc Perkin Trans. I 307-314 (1982) (—CH—CH—, cis and trans); Almquist et al. J. Med. Chem. 23:1392-1398 (1980) (—$COCH_2$—); Jennings-White et al. Tetrahedron Lett 23:2533 (1982) (—$COCH_2$—); Szelke et al. European Appln, EP 45665 CA (1982): 97:39405 (1982) (—CH(OH)$CH_2$—); Holladay et al. Tetrahedron. Lett 24:4401-4404 (1983) (—C (OH)CH$_2$—); and Hruby Life Sci 31:189-199 (1982) (—CH$_2$—S—); each of which is incorporated herein by reference. A particularly preferred non-peptide linkage is —CH$_2$NH—. It is understood that peptide analogs can have more than one atom between the bond atoms, such as b-alanine, g-aminobutyric acid, and the like.

Amino acid analogs and analogs and peptide analogs often have enhanced or desirable properties, such as, more economical production, greater chemical stability, enhanced pharmacological properties (half-life, absorption, potency, efficacy, etc.), altered specificity (e.g., a broad-spectrum of biological activities), reduced antigenicity, and others. See U.S. Pat. No. 6,358,922 issued Mar. 19, 2002 directed to positively-charged non-natural amino acids, methods of making and uses thereof in peptides.

D-amino acids can be used to generate more stable peptides, because D amino acids are not recognized by peptidases and such. Systematic substitution of one or more amino acids of a consensus sequence with a D-amino acid of the same type (e.g., D-lysine in place of L-lysine) can be used to generate more stable peptides. Cysteine residues can be used to cyclize or attach two or more peptides together. This can be beneficial to constrain peptides into particular conformations. (Rizo and Gierasch Ann. Rev. Biochem. 61:387 (1992), incorporated herein by reference).

The disclosed peptides can be mixed with, linked to or attached to other components to create a structure that contains the disclosed peptide (e.g, P4 or other similar epitopes). The peptide can be multi-valent as in a multiple antigenic peptide (See U.S. application Ser. No. 09/613,092 and Johnson et al. (The Journal of Infectious Diseases 2002; 185: 489-96), incorporated herein by reference for their teaching regarding how to make multiple antigenic peptides.) The peptide can also be in a fusion protein providing multiple copies of the peptide.

Mimetics

P4 peptide mimetics having a conformational structure identical or similar to the conformation of P4 (e.g., SEQ ID NO:1 and SEQ ID NO:2) are provided. A P4 mimetic also retains the PsaA receptor-binding function, and other functions disclosed herein, of SEQ ID NO:1. The mimetic can be a macromolecule (e.g., protein, nucleic acid, etc.) or it can be a small molecule.

The 3-D structure (conformation) of the P4 peptide is defined by its primary sequence, which in turn controls its secondary and tertiary structure. Examples of mimetics include SEQ ID NOS:7-15. Methods of identifying additional mimetics are described herein.

Three dimensional models are commonly available and are familiar to those skilled in the art. Computer programs are available which illustrate and display probable three-dimensional conformational structures of selected candidate mimetics. Inspection of these displays permits analysis of the likely role of the residues in the functioning of the candidate mimetic sequence, i.e., the analysis of residues that influence the ability of the candidate mimetic to retain its conformation. In this way, mimetics with differences in primary structure can be rationally prepared with a reasonable likelihood of retaining 3-D structure. Also, another approach is to use phage display to identify molecules that share the conformation (3-D structure) of P4. Examples of mimetics include the peptides P1 (SEQ ID NO:3) and P3 (SEQ ID NO:5), which were identified by phage display. Thus, while they have different primary structures (amino acid sequences) they share the conformation of, and, thus, the functional characteristics of P4 peptide.

Also provided is an antigen/peptide reagent kit comprising containers of the P4 peptide, variant or mimetic of the invention and one or more reagents for detecting binding of the antigen/peptide to an antibody to S. pneumoniae PsaA or P4 peptide. The reagents can include, for example, fluorescent tags, enzymatic tags, or other tags. The reagents can also include secondary or tertiary antibodies or reagents for enzymatic reactions, wherein the enzymatic reactions produce a product that can be visualized.

Antibodies

An antibody that specifically binds to the epitope defined by the disclosed peptides is provided. For example, the antibody can specifically bind to a peptide comprising the sequence set forth in SEQ ID NO:1 and having the conformation defined by the peptide consisting of SEQ ID NO:1. This isolated peptide represents the conformation of an immunodominant epitope of the native PsaA. An antibody that specifically binds to a peptide comprising the sequence set forth in SEQ ID NO:2 and having the conformation defined by the peptide consisting of SEQ ID NO:2 is also provided. This isolated peptide represents the conformation of an immunodominant epitope of the native PsaA. A P4-specific antibody is PsaA-specific since P4 defines an epitope specific for PsaA.

These antibodies are made by the usual means, including immunizing an animal with a peptide of the invention, for example by immunizing with the peptide of SEQ ID NO:1 or SEQ ID NO:2. Likewise, the peptides of SEQ ID NOS:3 (P1) and 5 (P3) are also immunogens for the preparation of an antibody that binds the epitope defined by the peptide of SEQ ID NO:1. The immunogenicity of P1, P2 and P3 is described in Johnson et al. (2002). An example of an antibody that binds to SEQ ID NO:1 is the antibody designated 8G12G11B10, or a fragment thereof which retains the binding characteristics of antibody 8G12G11B10. This monoclonal antibody is deposited with the American Type Culture Collection, 10801 University Blvd., Manassas Va., 20110-2209, under accession number PTA-6532.

As used herein, the term "antibody" encompasses, but is not limited to, whole immunoglobulin (i.e., an intact antibody) of any class. Thus it includes intact molecules as well as fragments thereof, such as, for example, Fab and F(ab')$_{21}$ which are capable of binding the epitopic determinant. Native antibodies are usually heterotetrameric glycoproteins, composed of two identical light (L) chains and two identical heavy (H) chains. Typically, each light chain is linked to a heavy chain by one covalent disulfide bond, while the number of disulfide linkages varies between the heavy chains of different immunoglobulin isotypes. Each heavy and light chain also has regularly spaced intrachain disulfide bridges. Each heavy chain has at one end a variable domain (V(H)) followed by a number of constant domains. Each light chain has a variable domain at one end (V(L)) and a constant domain at its other end; the constant domain of the light chain is aligned with the first constant domain of the heavy chain, and the light chain variable domain is aligned with the variable domain of the heavy chain. Particular amino acid residues are believed to form an interface between the light and heavy chain variable domains. The light chains of antibodies from any vertebrate species can be assigned to one of two clearly distinct types, called kappa (k) and lambda (l), based on the amino acid sequences of their constant domains. Depending on the amino acid sequence of the constant domain of their heavy chains, immunoglobulins can be assigned to different classes. There are five major classes of human immunoglobulins: IgA, IgD, IgE, IgG and IgM, and several of these may be further divided into subclasses (isotypes), e.g., IgG-1, IgG-2, IgG-3, and IgG-4; IgA-1 and IgA-2. One skilled in the art would recognize the comparable classes for mouse. The heavy chain constant domains that correspond to the different classes of immunoglobulins are called alpha, delta, epsilon, gamma, and mu, respectively.

The term "variable" is used herein to describe certain portions of the variable domains that differ in sequence among antibodies and are used in the binding and specificity of each particular antibody for its particular antigen. However, the variability is not usually evenly distributed through the variable domains of antibodies. It is typically concentrated in three segments called complementarity determining regions (CDRs) or hypervariable regions both in the light chain and the heavy chain variable domains. The more highly conserved portions of the variable domains are called the framework (FR). The variable domains of native heavy and light chains each comprise four FR regions, largely adopting a b-sheet configuration, connected by three CDRs, which form loops connecting, and in some cases forming part of, the b-sheet structure. The CDRs in each chain are held together in close proximity by the FR regions and, with the CDRs from the other chain, contribute to the formation of the antigen binding site of antibodies (see Kabat E. A. et al., "Sequences of Proteins of Immunological Interest," National Institutes of Health, Bethesda, Md. (1987)). The constant domains are not involved directly in binding an antibody to an antigen, but exhibit various effector functions, such as participation of the antibody in antibody-dependent cellular toxicity.

The term "monoclonal antibody" as used herein refers to an antibody obtained from a substantially homogeneous population of antibodies, i.e., the individual antibodies comprising the population are identical except for possible naturally occurring mutations that may be present in minor amounts. The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired activity (See, U.S. Pat. No. 4,816,567 and Morrison et al., Proc. Natl. Acad. Sci. USA, 81:6851-6855 (1984)).

Monoclonal antibodies are prepared using hybridoma methods, such as those described by Kohler and Milstein, Nature, 256:495 (1975) or Harlow and Lane. Antibodies, A Laboratory Manual. Cold Spring Harbor Publications, New York, (1988). In a hybridoma method, a mouse or other appropriate host animal, is typically immunized with an immunizing agent to elicit lymphocytes that produce or are capable of producing antibodies that will specifically bind to the immunizing agent. Alternatively, the lymphocytes may be immunized in vitro. In one example, the immunizing agent comprises a peptide disclosed herein (e.g., comprising SEQ ID NO:1 or SEQ ID NO:2). Traditionally, the generation of monoclonal antibodies has depended on the availability of purified protein or peptides for use as the immunogen. More recently DNA based immunizations have shown promise as a way to elicit strong immune responses and generate monoclonal antibodies. In this approach, DNA-based immunization can be used, wherein DNA encoding a portion of a disclosed peptide (e.g., comprising SEQ ID NO:1 or SEQ ID NO:2) expressed as a fusion protein with human IgG1 is injected into the host animal according to methods known in the art (e.g., Kilpatrick K E, et al. Gene gun delivered DNA-based immunizations mediate rapid production of murine monoclonal antibodies to the Flt-3 receptor. Hybridoma 1998 December; 17(6):569-76; Kilpatrick K E et al. High-affinity monoclonal antibodies to PED/PEA-15 generated using 5 micrograms of DNA. Hybridoma. 2000 August; 19(4):297-302, which are incorporated herein by referenced in full for the methods of antibody production).

An alternate approach to immunizations with either purified protein or DNA is to use antigen expressed in baculovirus. The advantages to this system include ease of generation, high levels of expression, and post-translational modifications that are highly similar to those seen in mammalian systems. Use of this system involves expressing domains of P4 antibody as fusion proteins. The antigen is produced by inserting a gene fragment in-frame between the signal sequence and the mature protein domain of the P4 antibody nucleotide sequence. This results in the display of the foreign proteins on the surface of the virion. This method allows immunization with whole virus, eliminating the need for purification of target antigens.

Generally, either peripheral blood lymphocytes ("PBLs") are used in methods of producing monoclonal antibodies if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, "Monoclonal Antibodies: Principles and Practice" Academic Press, (1986) pp. 59-103). Immortalized cell lines are usually transformed mammalian cells, including myeloma cells of rodent, bovine, equine, and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Rockville, Md. Human myeloma and mouse-human heteromycloma cell lines also have been described for the production of human monoclonal antibodies (Kozbor, J. Immunol., 133:3001 (1984); Brodeur et al., "Monoclonal Antibody Production Techniques and Applications" Marcel Dekker, Inc., New York, (1987) pp. 51-63). The culture medium in which the hybridoma cells are cultured can then be assayed for the presence of monoclonal antibodies directed against a disclosed peptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art, and are described further in the Examples below or in Harlow and Lane "Antibodies, A Laboratory Manual" Cold Spring Harbor Publications, New York, (1988).

After the desired hybridoma cells are identified, the clones may be subcloned by limiting dilution or FACS sorting procedures and grown by standard methods. Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, protein G, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies can be readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as simian COS cells, Chinese hamster ovary (CHO) cells, plasmacytoma cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816,567), or by covalently joining to the immunoglobulin coding sequence all or part of the coding sequence for a non-immunoglobulin polypeptide. Optionally, such a non-immunoglobulin polypeptide is substituted for the constant domains of an antibody or substituted for the variable domains of one antigen-combining site of an antibody to create a chimeric bivalent antibody comprising one antigen-combining site having specificity for P4 and another antigen-combining site having specificity for a different antigen.

Transgenic animals (e.g., mice) that are capable, upon immunization, of producing a full repertoire of human antibodies in the absence of endogenous immunoglobulin production can be employed. For example, it has been described that the homozygous deletion of the antibody heavy chain joining region (J(H)) gene in chimeric and germ-line mutant mice results in complete inhibition of endogenous antibody production. Transfer of the human germ-line immunoglobulin gene array in such germ-line mutant mice will result in the production of human antibodies upon antigen challenge (see, e.g., Jakobovits et al., Proc. Natl. Acad. Sci. USA, 90:2551-255 (1993); Jakobovits et al., Nature, 362:255-258 (1993); Bruggemann et al., Year in Immuno., 7:33 (1993)). Human antibodies can also be produced in phage display libraries (Hoogenboom et al., J. Mol. Biol., 227:381 (1991); Marks et al., J. Mol. Biol., 222:581 (1991)). The techniques of Cote et al. and Boerner et al. are also available for the preparation of human monoclonal antibodies (Cole et al., Monoclonal Antibodies and Cancer Therapy, Alan R. Liss, p. 77 (1985); Boerner et al., J. Immunol., 147(1):86-95 (1991)).

As used herein, the term "antibody or fragments thereof" encompasses chimeric antibodies and hybrid antibodies, with dual or multiple antigen or epitope specificities, and fragments, such as F(ab')2, Fab', Fab and the like, including hybrid fragments. Thus, fragments of the antibodies that retain the ability to bind their specific antigens are provided. For example, fragments of antibodies which maintain P4/PsaA binding activity are included within the meaning of the term "antibody or fragment thereof." Such antibodies and fragments can be made by techniques known in the art and can be screened for specificity and activity according to the methods set forth in the Examples and in general methods for producing antibodies and screening antibodies for specificity and activity (See Harlow and Lane. Antibodies, A Laboratory Manual. Cold Spring Harbor Publications, New York, (1988)).

Also included within the meaning of "antibody or fragments thereof" are conjugates of antibody fragments and antigen binding proteins (single chain antibodies) as described, for example, in U.S. Pat. No. 4,704,692, the contents of which are hereby incorporated by reference.

An isolated immunogenically specific paratope or fragment of the antibody is also provided. A specific immunogenic epitope of the antibody can be isolated from the whole antibody by chemical or mechanical disruption of the molecule. The purified fragments thus obtained are tested to determine their immunogenicity and specificity by the methods taught herein. Immunoreactive paratopes of the antibody, optionally, are synthesized directly. An immunoreactive fragment is defined as an amino acid sequence of at least about two to five consecutive amino acids derived from the antibody amino acid sequence.

Alternatively, unprotected peptide segments are chemically linked where the bond formed between the peptide segments as a result of the chemical ligation is an unnatural (non-peptide) bond (Schnolzer, M et al. Science; 256:221 (1992)). This technique has been used to synthesize analogs of protein domains as well as large amounts of relatively pure proteins with full biological activity (deLisle Milton R C et al., Techniques in Protein Chemistry IV. Academic Press, New York, pp. 257-267 (1992)).

Also disclosed are fragments of antibodies which have bioactivity. The polypeptide fragments can be recombinant proteins obtained by cloning nucleic acids encoding the polypeptide in an expression system capable of producing the polypeptide fragments thereof, such as an adenovirus or baculovirus expression system. For example, one can determine the active domain of an antibody from a specific hybridoma that can cause a biological effect associated with the interaction of the antibody with P4 or PsaA. For example, amino acids found to not contribute to either the activity or the binding specificity or affinity of the antibody can be deleted without a loss in the respective activity. For example, in various embodiments, amino or carboxy-terminal amino acids are sequentially removed from either the native or the modified non-immunoglobulin molecule or the immunoglobulin molecule and the respective activity assayed in one of many available assays. In another example, a fragment of an antibody comprises a modified antibody wherein at least one amino acid has been substituted for the naturally occurring amino acid at a specific position, and a portion of either amino terminal or carboxy terminal amino acids, or even an internal region of the antibody, has been replaced with a polypeptide fragment or other moiety, such as biotin, which can facilitate in the purification of the modified antibody. For example, a modified antibody can be fused to a maltose binding protein, through either peptide chemistry or cloning the respective nucleic acids encoding the two polypeptide fragments into an expression vector such that the expression of the coding region results in a hybrid polypeptide. The hybrid polypeptide can be affinity purified by passing it over an amylose affinity column, and the modified antibody receptor can then be separated from the maltose binding region by cleaving the hybrid polypeptide with the specific protease factor Xa. (See, for example, New England Biolabs Product Catalog, 1996, pg. 164.). Similar purification procedures are available for isolating hybrid proteins from eukaryotic cells as well.

The fragments, whether attached to other sequences or not, include insertions, deletions, substitutions, or other selected modifications of particular regions or specific amino acids residues, provided the activity of the fragment is not significantly altered or impaired compared to the nonmodified antibody or antibody fragment. These modifications can provide for some additional property, such as to remove or add amino acids capable of disulfide bonding, to increase its bio-longevity, to alter its secretory characteristics, etc. In any case, the fragment must possess a bioactive property, such as binding activity, regulation of binding at the binding domain, etc. Functional or active regions of the antibody may be identified by mutagenesis of a specific region of the protein, followed by expression and testing of the expressed polypeptide. Such methods are readily apparent to a skilled practitioner in the art and can include site-specific mutagenesis of the nucleic acid encoding the antigen. (Zoller M J et al. Nucl. Acids Res. 10:6487-500 (1982).

Techniques can also be adapted for the production of single-chain antibodies specific to an antigenic protein of the invention (see e.g., U.S. Pat. No. 4,946,778). In addition, methods can be adapted for the construction of F (ab) expression libraries (see e.g., Huse, et al., 1989 Science 246: 1275-1281) to allow rapid and effective identification of monoclonal F (ab) fragments with the desired specificity for a protein or derivatives, fragments, analogs or homologs thereof. Antibody fragments that contain the idiotypes to a protein antigen may be produced by techniques known in the art including, but not limited to: (i) an F ((ab'))(2) fragment produced by pepsin digestion of an antibody molecule; (ii) an Fab fragment generated by reducing the disulfide bridges of an F ((ab'))(2) fragment; (iii) an F (ab) fragment generated by the treatment of the antibody molecule with papain and a reducing agent and (iv) F (v), fragments.

Methods for the production of single-chain antibodies are well known to those of skill in the art. The skilled artisan is referred to U.S. Pat. No. 5,359,046 (incorporated herein by reference) for such methods. A single chain antibody is created by fusing together the variable domains of the heavy and light chains using a short peptide linker, thereby reconstituting an antigen binding site on a single molecule. Single-chain antibody variable fragments (scFvs) in which the C-terminus of one variable domain is tethered to the N-terminus of the other variable domain via a 15 to 25 amino acid peptide or linker have been developed without significantly disrupting antigen binding or specificity of the binding (Bedzyk et al., 1990; Chaudhary et al., 1990). The linker is chosen to permit the heavy chain and light chain to bind together in their proper conformational orientation. See, for example, Huston, J. S., et al., Methods in Enzym. 203:46-121 (1991), which is incorporated herein by reference. These Fvs lack the constant regions (Fe) present in the heavy and light chains of the native antibody.

In vitro methods are also suitable for preparing monovalent antibodies. Digestion of antibodies to produce fragments thereof, particularly, Fab fragments, can be accomplished using routine techniques known in the art. For instance, digestion can be performed using papain. Examples of papain digestion are described in WO 94/29348 published Dec. 22, 1994, U.S. Pat. No. 4,342,566, and Harlow and Lane, Antibodies, A Laboratory Manual, Cold Spring Harbor Publications, New York, (1988). Papain digestion of antibodies typically produces two identical antigen binding fragments, called Fab fragments, each with a single antigen binding site, and a residual Fc fragment. Pepsin treatment yields a fragment, called the F(ab')2 fragment, that has two antigen combining sites and is still capable of cross-linking antigen.

The Fab fragments produced in the antibody digestion also contain the constant domains of the light chain and the first constant domain of the heavy chain. Fab' fragments differ from Fab fragments by the addition of a few residues at the carboxy terminus of the heavy chain domain including one or more cysteines from the antibody hinge region. The F(ab')2 fragment is a bivalent fragment comprising two Fab' fragments linked by a disulfide bridge at the hinge region. Fab'-SH is the designation herein for Fab' in which the cysteine residue(s) of the constant domains bear a free thiol group. Antibody fragments originally were produced as pairs of Fab' fragments which have hinge cysteines between them. Other chemical couplings of antibody fragments are also known.

In hybrid antibodies, one heavy and light chain pair is homologous to that found in an antibody raised against one antigen recognition feature, e.g., epitope, while the other heavy and light chain pair is homologous to a pair found in an antibody raised against another epitope. This results in the property of multi-functional valency, i.e., ability to bind at least two different epitopes simultaneously. Such hybrids can be formed by fusion of hybridomas producing the respective component antibodies, or by recombinant techniques. As used herein, the term "hybrid antibody" refers to an antibody wherein each chain is separately homologous with reference to a mammalian antibody chain, but the combination represents a novel assembly so that two different antigens are recognized by the antibody.

Antibody humanization techniques generally involve the use of recombinant DNA technology to manipulate the DNA sequence encoding one or more polypeptide chains of an antibody molecule. Accordingly, a humanized form of a non-human antibody (or a fragment thereof) is a chimeric antibody or antibody chain (or a fragment thereof, such as an Fv, Fab, Fab', or other antigen-binding portion of an antibody) which contains a portion of an antigen binding site from a non-human (donor) antibody integrated into the framework of a human (recipient) antibody.

To generate a humanized antibody, residues from one or more complementarity determining regions (CDRs) of a recipient (human) antibody molecule are replaced by residues from one or more CDRs of a donor (non-human) antibody molecule that is known to have desired antigen binding characteristics (e.g., a certain level of specificity and affinity for the target antigen). In some instances, Fv framework (FR) residues of the human antibody are replaced by corresponding non-human residues. Humanized antibodies may also contain residues which are found neither in the recipient antibody nor in the imported CDR or framework sequences. Generally, a humanized antibody has one or more amino acid residues introduced into it from a source which is non-human. In practice, humanized antibodies are typically human antibodies in which some CDR residues and possibly some FR residues are substituted by residues from analogous sites in rodent antibodies. Humanized antibodies generally contain at least a portion of an antibody constant region (Fc), typically that of a human antibody (Jones et al., Nature, 321:522-525 (1986), Reichmann et al., Nature, 332:323-327 (1988), and Presta, Curr. Opin. Struct. Biol., 2:593-596 (1992)).

Methods for humanizing non-human antibodies are well known in the art. For example, humanized antibodies can be generated according to the methods of Winter and co-workers (Jones et al., Nature, 321:522-525 (1986), Riechmann et al., Nature, 332:323-327 (1988), Verhoeyen et al., Science, 239: 1534-1536 (1988)), by substituting rodent CDRs or CDR sequences for the corresponding sequences of a human antibody. Methods that can be used to produce humanized antibodies are also described in U.S. Pat. No. 4,816,567 (Cabilly et al.), U.S. Pat. No. 5,565,332 (Hoogenboom et al.), U.S. Pat. No. 5,721,367 (Kay et al.), U.S. Pat. No. 5,837,243 (Deo et al.), U.S. Pat. No. 5,939,598 (Kucherlapati et al.), U.S. Pat. No. 6,130,364 (Jakobovits et al.), and U.S. Pat. No. 6,180,377 (Morgan et al.).

Also provided is an antibody reagent kit comprising containers of the monoclonal antibody or fragment thereof of the invention and one or more reagents for detecting binding of the antibody or fragment thereof to S. pneumoniae PsaA or P4 peptide. The reagents can include, for example, fluorescent tags, enzymatic tags, or other tags. The reagents can also include secondary or tertiary antibodies or reagents for enzymatic reactions, wherein the enzymatic reactions produce a product that can be visualized.

Vaccines

A vaccine comprising the peptide of SEQ ID NO:1 and a pharmaceutical carrier is provided. A vaccine comprising a peptide of SEQ ID NO:2 and a pharmaceutical carrier is also provided.

The immunogenic peptides disclosed herein can be used in the construction of a vaccine comprising an immunogenic amount of the antigen and a pharmaceutically acceptable carrier. The vaccine can be a peptide of the present invention or the peptide bound to a carrier or a mixture of bound or unbound peptide. The vaccine can then be used in a method of preventing S. pneumoniae infection.

Immunogenic amounts of the peptide can be determined using standard procedures. Briefly, various concentrations of a putative specific immunoreactive peptides or polypeptides are prepared, administered to an animal and the immunological response (e.g., the production of antibodies or cell-mediated response) of an animal to each concentration is determined. The vaccine composition can also comprise an adjuvant.

Pharmaceutical Compositions

The disclosed compositions (e.g., P4 peptides and P4-specific antibodies) can also be administered in vivo in a pharmaceutically acceptable carrier.

The pharmaceutical compositions of the invention include an effective amount of the P4 peptide, peptide mimetic, P4 antibody or PsaA receptor. Effective amounts of the disclosed P4 peptide in the composition range from 0.1 µg to 1.0 mg, for example from to 2 µg to 500 µg or from 2.5 to 5 µg, measured per kilogram of body weight. For antibodies, and effective dose includes a titer of ≧100 for human sera with at least 50% inhibition of PsaA adherence or at least 30% inhibition of pneumococcal adherence as measured in assays disclosed herein. For example, dosages of from 0.02 mg/kg to 0.5 mg/kg or from 0.005 mg/kg to 0.025 mg/kg can be administered.

By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

Pharmaceutical carriers are known to those skilled in the art. These most typically would be standard carriers for administration of drugs to humans, including solutions such as sterile water, saline, and buffered solutions at physiological pH. The compositions can be administered according to standard procedures used by those skilled in the art as further described herein.

Suitable carriers and their formulations are described in *Remington: The Science and Practice of Pharmacy* (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semi-permeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, anti-inflammatory agents, anesthetics, and the like.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, antioxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. These formulations can include chewing gum, lozenges oral gels or tooth pastes.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

The pharmaceutically acceptable carrier in a vaccine composition can comprise saline or other suitable carriers (Arnon, R. (Ed.) Synthetic Vaccines 1:83-92, CRC Press, Inc., Boca Raton, Fla., 1987). An adjuvant or mixture of adjuvants can also be a part of the carrier of the vaccine, in which case it can be selected by standard criteria based on the antigen used, the mode of administration and the subject (Arnon, R. (Ed.), 1987). An "adjuvant" is a composition that enhances the immunogenic activity of an immunogenic substance when administered in conjunction with that substance. Adjuvants can include TiterMax™ adjuvant, aluminum hydroxide or aluminum phosphate as an adjuvant. Examples of adjuvants that can be used for intranasal administration include the following: 1) Cholera toxin subunit B (CTB), 2) CpG—cytosine phosphate guanosine dideoxynucleotide, 3) chitosan, 4) Muramydi-peptide (MDP), 5) Cell-invasive adenylate cyclase toxin from *Bordetella pertussis*, and 6) PEG (polyethylene glycol). One of ordinary skill in the art would be able to identify other antigens or immunogens, and immunomodulators, such as cytokines, appropriate for the present pharmaceutical compositions. Methods of administration can be by oral or sublingual means, or by injection, depending on the particular vaccine used and the subject to whom it is administered.

Receptor

The receptor for PsaA is disclosed herein as the binding partner of peptide P4. Having disclosed P4 as receptor-binding domain of PsaA, a conformation that defines the receptor is essentially structurally defined as the 3-dimensional match for P4. PsaA contacts a cell by binding or attaching to the cell receptor that PsaA binds to. The cell receptor can be structurally complex, comprising a complex of multiple subunits, not just a single component. The receptor can be characterized as an intercellular adhesion molecule as suggested by the pattern of PsaA bead binding to NP cells (FIG. 1). A mechanism similar to internalin (*Listeria monocytogenes*) binding to E-cadherin is a potential mechanism for the biding of PsaA/P4 to NP cells.

PsaA receptor mimetics share the essential conformational structure defined by the P4 peptide, and are either identical or similar to the native PsaA-binding domain of the PsaA cellular receptor(s). The mimic can be a PsaA-binding domain of the native PsaA receptor, i.e., the region that interacts with a P4 peptide. Thus, the mimetic can be a P4-binding fragment of the PsaA receptor. The receptor/receptor mimic can be used for diagnostic assays or functional assays of antibodies elicited after infection and/or vaccination.

The receptor can be a native (naturally occurring) protein present on a cell on which it naturally occurs. The receptor or receptor mimic can be recombinantly expressed at selected amounts on a cell that does not naturally express it or it can be over-expressed on a cell that naturally expresses the receptor.

Methods of Preventing and Treating Infection

A method of inhibiting binding of pneumococcal surface adhesin protein A (PsaA) to cells that express a PsaA receptor is provided, comprising contacting the cell with a P4 peptide described herein. For example, the P4 peptide can comprise or consist of the peptide of SEQ ID NO:1 or variants or analogs thereof, or the peptide can comprise or consist of the peptide of SEQ ID NO:2 or variants or analogs thereof.

The P4 peptide can, alternatively, comprise or consist of the peptide of SEQ ID NO:3 or variants or analogs thereof, or the peptide can comprise or consist of the peptide of SEQ ID NO:5 or variants or analogs thereof.

The terms "binding" and "attachment" are used herein to describe the typical interaction of a ligand to its receptor or an antibody-antigen interaction.

The disclosed method of inhibiting binding is applicable to any target cell expressing a PsaA receptor or receptor mimic, for example, pneumocytes, epithelial or endothelial cells. The target cells for *S. pneumoniae* infection can be mucosal cells or airway cells, among others. A particularly relevant class of cells is the nasopharyngeal epithelial cells, which are a natural reservoir for *S. pneumoniae*. Any cell type that expresses the PsaA receptor can be identified using the P4 binding protocols described herein. This includes naturally occurring PsaA receptor and receptor expressed by cells transformed with a PsaA receptor-expressing nucleic acid.

Specifically provided is a method of inhibiting binding of or attachment of PsaA to nasopharyngeal epithelial cells, comprising contacting the cell with a P4 peptide, for example, a peptide comprising or consisting of the peptide of SEQ ID NO:1 or variants or analogs thereof, or a peptide comprising or consisting of the peptide of SEQ ID NO:2 or variants or analogs thereof.

A method of inhibiting binding *S. pneumoniae* to cells that express a PsaA receptor is provided, comprising contacting the cell with a P4 peptide. For example, the P4 peptide can comprise or consist of the peptide of SEQ ID NO:1 or variants or analogs thereof, or the peptide can comprise or consist of the peptide of SEQ ID NO:2 or variants or analogs thereof.

Specifically provided is a method of inhibiting binding of or attachment of *S. pneumoniae* to nasopharyngeal epithelial cells, comprising contacting the cell with a P4 peptide, for example, a peptide comprising or consisting of the peptide of SEQ ID NO:1 or variants or analogs thereof, or a peptide comprising or consisting of the peptide of SEQ ID NO:2 or variants or analogs thereof.

A method of inhibiting binding of a transparent *S. pneumoniae* to cells that express a PsaA receptor and enhancing the uptake of the bacterium is provided, comprising contacting the cell with a P4 peptide. For example, the P4 peptide can comprise or consist of the peptide of SEQ ID NO:1 or variants or analogs thereof, or the peptide can comprise or consist of the peptide of SEQ ID NO:2 or variants or analogs thereof. *S. pneumoniae* undergoes spontaneous phase variation in colony morphology. Differences in colony opacity have previously been shown to correlate with differences in the ability of organisms to colonize the mucosal surface of the nasopharynx in an animal model. The transparent phenotype colonizes tissue in the nasopharynx. Once opaque, the bacterium is taken up (internalized) by phagocytosis in the presence of P4 peptide.

P4 can act as a signal transducer, causing epithelial cells to up-regulate and become active phagocytic cells so that engulfment is augmented. This allows for the opaque phenotype to by internalized. Thus, a method of enhancing internalization of pneumococci by contacting cells of the nasopharynx with a P4 peptide is provided. Since the binding of PsaA to cell receptors triggers other events that are unique to the interaction of PsaA or P4 and cell receptors, these events are triggered by the disclosed P4 peptides. For example, reduction in IL-8, IL-16 and EGF are noted. Membrane ruffling and changes in membrane associated protein profiles are also seen in eukaryotic cells. Thus, the recognized downstream events of PsaA contact with its receptor are stimulated by contact of a disclosed P4 peptide with cells.

A method of increasing expression of a cytokine by a cell, comprising administering a P4 peptide to the cell is provided. FGFbasic is a cytokine that plays an important role in tissue differentiation and, angiogenesis in the embryonic stage. Further, this cytokine has the unique ability to augment neural cell development and wound healing. FGFbasic produced by P4 treated cells enhances the growth of fibroblasts. Thus, an increase in FGFbasic as shown herein can hasten wound healing.

A method of decreasing expression of a cytokine by a cell, comprising administering a P4 peptide is provided. The decrease is exemplified herein with IL-8, IL-16 and EGF. EGF is a C—X—C type chemokine that plays the major role in the transformation of benign tumor in to malignant. This is effected by down regulating the expression of E-cadherin, the junction glue that binds and maintains the cellular integrity with the adjoining cells. In tumor cells, an enhanced production of EGF leads to down regulation of E-cadherin expression that in turn initiates tumor metastasis. P4 peptide treatment brings down EGF production in the treated cells in a dose dependent manner. Hence, this peptide can play a major role in reversing or delaying tumor metastasis.

Anti-P4 antibodies are shown herein to inhibit the binding of P4 to cells. Thus, a method of inhibiting binding of PsaA to cells that express a PsaA receptor is provided, comprising contacting the PsaA with a P4-specific antibody described herein. For example, the antibody can be specific for a P4 peptide comprising or consisting of the peptide of SEQ ID NO:1 or variants or analogs thereof.

A method of inhibiting binding of PsaA to cells that express a PsaA receptor is provided, comprising contacting the PsaA with a P4-specific antibody described herein. For example, the antibody can be specific for a P4 peptide comprising or consisting of the peptide of SEQ ID NO:2 or variants or analogs thereof.

Specifically provided is a method of inhibiting binding of or attachment of PsaA to nasopharyngeal epithelial cells, comprising contacting the cell with a P4-specific antibody described herein. For example, the antibody can be specific for a peptide comprising or consisting of the peptide of SEQ ID NO:1 or variants or analogs thereof, or an antibody specific for a P4 peptide comprising or consisting of the peptide of SEQ ID NO:2 or variants or analogs thereof.

A method of inhibiting binding of S. pneumoniae to cells that express a PsaA receptor is provided, comprising contacting the S. pneumoniae with a P4-specific antibody described herein. For example, the antibody can be specific for a P4 peptide comprising or consisting of the peptide of SEQ ID NO:1 or variants or analogs thereof.

A method of inhibiting binding of S. pneumoniae to cells that express a PsaA receptor is provided, comprising contacting the S. pneumoniae with a P4-specific antibody described herein. For example, the antibody can be specific for a P4 peptide comprising or consisting of the peptide of SEQ ID NO:2 or variants or analogs thereof.

Specifically provided is a method of inhibiting binding of or attachment of S. pneumoniae to nasopharyngeal epithelial cells, comprising contacting the cell with a P4-specific antibody described herein. For example, the antibody can be specific for a peptide comprising or consisting of the peptide of SEQ ID NO:1 or variants or analogs thereof, or an antibody specific for a P4 peptide comprising or consisting of the peptide of SEQ ID NO:2 or variants or analogs thereof.

A method of inhibiting binding of PsaA to a target cell expressing a PsaA receptor is provided, comprising contacting the PsaA with an isolated or soluble PsaA receptor or P4-binding domain (fragment) thereof. The PsaA binding site on the receptor (i.e., are receptor fragment) can also be isolated. The solubilized receptor or PsaA binding can be used as a blocker of PsaA binding to cells. The effectiveness of a region of the PsaA receptor as a blocker of S. pneumoniae binding to a cell is determined using the standard blocking assays disclosed herein and in the art.

In the methods of inhibiting binding of PsaA to cells expressing a PsaA receptor, the PsaA can be on the S. pneumoniae bacterial cell (e.g., for treating/preventing an infection or research use). Thus, provided is a method for treating or preventing S. pneumoniae infection, comprising inhibiting the binding of PsaA to cells expressing a PsaA receptor using a P4 peptide or antibody thereto. The terms "treat," "treatment" or "treating" mean to administer a composition to a subject with a condition, wherein the condition can be any pathologic disease, cancer, infection, or inflammatory condition. The effect of the administration to the subject can have the effect of but is not limited to reducing the symptoms of the condition, a reduction in the severity of the condition, or the complete ablation of the condition. By "prevent," "prevention" or "preventing" is meant to minimize the chance that a subject will develop a disease or condition resulting from S. pneumoniae infection. A "subject" is an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and more preferably, a human.

In the method of preventing or treating an S. pneumoniae infection, a vaccine comprising a P4 peptide (e.g., the peptide of SEQ ID NO:1 or a variant thereof) is administered to a subject in an immunization protocol. The immunization results in the production of anti-S. pneumoniae antibodies. These antibodies are also anti-PsaA and anti-P4 antibodies. The antibodies produced in the subject as a result of immunization reduce the bacterial carriage load in the subject, particularly in the nasopharynx where S. pneumoniae tends to be carried. In some instances, the immunization results in complete eradication of S. pneumoniae. In other instances, the immunization results in a measurable decrease in the amount of S. pneumoniae present in the subject. Thus, the treatment can result in protective immunity. As used herein "protective immunity" refers to a state in which a subject has generated antibodies, at least some of which are neutralizing antibodies, in response to exposure to a pathogen-related immunogen (e.g., a P4 peptide). Neutralizing antibodies bind the immunogenic component of the S. pneumoniae in such a way that proliferative infection is inhibited or abrogated, such that the subject is essentially free of symptomatic disease or has reduced symptoms. Protective immunity may also arise from an alternative immunogenic response which leads to inactivation, loss, or destruction of the pathogenic agent. When conducted prior to exposure to S. pneumoniae, the immunization method prevents infection (measured as no significant bacterial load recovered from the NP), or it results in a measurable decrease in the amount of S. pneumoniae present in the subject (measured as a reduction in bacterial load recovered from the NP as compared to controls).

In the method of preventing or treating an S. pneumoniae infection, a composition comprising an anti-P4 antibody (e.g., an antibody specific for the peptide of SEQ ID NO:1 or a variant thereof) is administered to a subject in an immunization protocol. This method of passive immunization results in the presence of anti-S. pneumoniae antibodies in the subject. These antibodies are also anti-PsaA and anti-P4 antibodies. The antibodies reduce the bacterial carriage load in the subject, particularly in the nasopharynx where S. pneumoniae tends to be carried. In some instances, the immunization results in complete eradication of S. pneumoniae. In other instances, the immunization results in a measurable decrease in the amount of S. pneumoniae present in the subject. When conducted prior to exposure to S. pneumoniae, the passive immunization method prevents infection (measured as no significant bacterial load recovered from the NP) or it results in a measurable decrease in the amount of S. pneumoniae present in the subject (measured as a reduction in bacterial load recovered from the NP as compared to controls).

Based on their sequence similarity to P4 of S. pneumoniae in the homologous protein, infection by other bacteria, including S. mitis, S. oralis, S. sanguis, S. parasanguis, S. agalacteae, S. pyogenes, Bacillus anthracis, Liseria monocytogenes, etc.) is treated or prevented.

In the methods of inhibiting binding of PsaA to cells expressing a PsaA receptor, the PsaA can be an isolated protein (e.g., for research use). Thus, a method of using a P4 peptide to study the interaction of S. pneumoniae and PsaA with cells is disclosed. Also provided is a method of using a P4-specific antibody to study the interaction of S. pneumoniae and PsaA with cells is disclosed.

In the disclosed methods, the disclosed compositions can be used therapeutically in combination with a pharmaceutically acceptable carrier.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intranasally, intravenously, intraperitoneally, intramuscularly, subcutaneously, intracavity, transdermally or by inhalation.

Intranasal delivery can be by topical intranasal administration or administration by inhalant. As used herein, "topical intranasal administration" means delivery of the compositions into the nose or nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

The materials may be in solution, suspension (for example, incorporated into microparticles, liposomes, or cells). These may be targeted to a particular cell type via antibodies, receptors, or receptor ligands.

When used in the above or other treatments, a therapeutically effective amount of one of the compounds (e.g., P4 peptide or P4 antibody) of the present invention may be employed in pure form or, where such forms exist, in pharmaceutically acceptable salt form and with or without a pharmaceutically acceptable excipient.

The specific therapeutically effective dose level for any particular patient will depend upon one or more factors including the disorder being treated and the severity of the disorder; activity of the specific compound employed; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts. Thus, it is not possible to specify an exact amount for every composition. However, an appropriate amount can be determined by one of ordinary skill in the art using only routine experimentation given the teachings herein. For example, it is well within the skill of the art to start doses of the compound at levels lower than those required to achieve the desired therapeutic effect and to gradually increase the dosage until the desired effect is achieved. If desired, the effective daily dose may be divided into multiple doses for purposes of administration. Consequently, single dose compositions may contain such amounts or submultiples thereof to make up the daily dose.

The dosage can be adjusted by the individual physician in the event of any counterindications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., Handbook of Monoclonal Antibodies, Ferrone et al., eds., Noges Publications, Park Ridge, N.J., (1985) ch. 22 and pp. 303-357; Smith et al., Antibodies in Human Diagnosis and Therapy, Haber et al., eds., Raven Press, New York (1977) pp. 365-389. A typical daily dosage of the P4 peptide used alone might range from about 0.1 µg to 0.1 mg per kilogram of body weight per day, for example from about 2.5 to 5 µg per kilogram of body weight per day, depending on the factors mentioned above.

In the methods of inhibiting binding by administering the peptides and antibodies disclosed herein, additional peptides or antibodies directed to other streptococci or gram negative bacteria can be administered. In this manner, both S. pneumoniae infection and other streptococcal infections (e.g., S. mitis, S. oralis, S. sanguis, S. parasanguis, S. agalacteae, S. pyogenes, Bacillus anthracis, Liseria monocytogenes, etc.) are treated or prevented.

Screening Methods

A method of identifying an antibody that inhibits or blocks binding of pneumococcal surface adhesin protein A (PsaA) to cells that express a PsaA receptor is provided. The method comprises: a) contacting the cells with PsaA and a P4 peptide in the presence or absence of the putative inhibiting antibody; and b) determining the amount of binding of the P4 peptide to the cells in the presence and absence of the putative inhibiting antibody, whereby a reduced amount of binding of the P4 peptide in the presence of the antibody compared to the amount of binding of the P4 peptide in the absence of the antibody identifies the antibody as an antibody that blocks binding of pneumococcal PsaA to the cells.

A method of identifying an antibody that inhibits or blocks binding of S. pneumoniae to cells that express a PsaA receptor is provided. In one example, the method comprises: a) contacting the cells with PsaA and a P4 peptide in the presence or absence of the putative inhibiting antibody; and b) determining the amount of binding of the P4 peptide to the cells in the presence and absence of the putative inhibiting antibody, whereby a reduced amount of binding of the P4 peptide in the presence of the antibody compared to the amount of binding of the P4 peptide in the absence of the antibody identifies the antibody as an antibody that blocks binding of pneumococcal PsaA to a S. pneumoniae to epithelial cells. In the method of identifying an antibody that blocks binding of S. pneumoniae to cells, the PsaA can be isolated (i.e., the PsaA is not on a bacterial cell). Alternatively, the PsaA can be expressed on an S. pneumoniae cell.

A method of detecting anti-S. pneumoniae antibodies in a subject or in a sample from a subject is provided. Since the P4 peptide represents an epitope of the PsaA protein of S. pneumoniae, it can be used to detect anti-S. pneumoniae antibodies. Thus, a method for diagnosing current or previous S. pneumoniae infection is provided. Protocols for detecting binding between the P4 peptide and anti-S. pneumoniae antibodies are exemplified herein. The methods using P4 are essentially the same as methods using PsaA to detect anti-S.

*pneumoniae* antibodies, which are known in the art. The present method has the advantage of the use of a smaller peptide, e.g., a P4 peptide in the detection assays.

The diagnostic and other detection methods disclosed can make use of selective binding of an antibody to an antigen. Selective binding to an antibody under such conditions may require an antibody that is selected for its specificity for a particular protein, proteoglycan, or variant, fragment, or protein core thereof. A variety of immunoassay formats may be used to select antibodies that selectively bind with P4 peptide or variant thereof. For example, solid-phase ELISA immunoassays are routinely used to select antibodies selectively immunoreactive with a peptide See Harlow and Lane. Antibodies, A Laboratory Manual. Cold Spring Harbor Publications, New York, (1988), for a description of immunoassay formats and conditions that could be used to determine selective binding. The binding affinity of a monoclonal antibody can, for example, be determined by the Scatchard analysis of Munson et al., Anal. Biochem., 107:220 (1980).

Having provided the P4 peptide and shown that it binds to the PsaA receptor on cells, a method of screening for other PsaA receptors is provided. The method can comprise contacting putative receptor-expressing cells with P4 linked to a detectable moiety and detecting the presence of label on the cell, the presence of label indicating the presence of a P4 receptor. The method can be used with intact cells or membrane fractions of cells to facilitate the isolation of the receptor protein. For example, P4 can be used in mobility shift assays to identify the cell receptor of PsaA. It can also be used to up-regulate the expression of the cell receptor.

As used herein, the term "detectable moiety" any means for detecting an interaction between a tag and a binding partner, thereby identifying the presence of the tag and the existence of the structural or synthetic information that the tag represents. The label may be any means of detection that can be assayed. The label provides a "signal" indicating which tag is being identified. These include, but not limited to, enzymes, fluorophores, biotin, chromophores, radioisotopes, colored particles, electrochemical, chemical-modifying or chemiluminescent moieties. A currently preferred detectable moiety is a fluorescent moiety. Common fluorescent moieties include: fluorescein, cyanine dyes, coumarins, phycoerythrin, phycobiliproteins, dansyl chloride, Texas Red, and lanthanide complexes. Of course, the derivatives of these compounds which are known to those skilled in the art also are included as common fluorescent moieties. Other examples include enzymes which can catalyze color or light emitting (luminescence) reactions. The detection of the detectable moiety can be direct provided that the detectable moiety is itself detectable, such as, for example, in the case of fluorophores. Alternatively, the detection of the detectable moiety can be indirect. In the latter case, a second moiety reactable with the detectable moiety, itself being directly detectable is preferably employed. The detectable moiety may be inherent to the molecular probe. For example, the constant region of an antibody can serve as an indirect detectable moiety to which a second antibody having a direct detectable moiety can specifically bind.

Provided is a method for identifying a mimetic of a PsaA receptor. Since the conformation of the receptor is known from the conformation of P4, mimetics are also defined by the presence of a structure complementary to the P4 peptide. These are routinely identified and isolated base on their binding to the P4 peptide. Using the methods described herein and elsewhere, molecules can be prepared and their binding to P4 confirmed.

Provided is a method for identifying a mimetic of a P4 peptide. The method can be used to identify and produce peptides and small molecules that retain the key structural features of P4, e.g, the conformation of P4. By "small molecules" is meant natural or synthetic organic molecules less than about 5 kD and most preferably less than about 4 kD. Small molecules can be nucleic acids, peptides, polypeptides, peptidomimetics, carbohydrates, lipids or other organic (carbon containing) or inorganic molecules.

An example of a way to isolate molecules that mimic P4 or the PsaA receptor is through rational design. This is achieved through structural information and computer modeling. Computer modeling technology allows visualization of the three-dimensional atomic structure of a selected molecule and the rational design of new compounds that will interact with the molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

Examples of molecular modeling systems are the CHARm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other.

A number of articles review computer modeling of drugs interactive with specific proteins, such as Rotivinen, et al., 1988 Acta Pharmaceutica Fennica 97, 159-166; Ripka, New Scientist 54-57. (Jun. 16, 1988); McKinaly and Rossmann, 1989 Annu. Rev. Pharmacol. Toxiciol. 29, 111-122; Perry and Davies, QSAR: Quantitative Structure-Activity Relationships in Drug Design pp. 189-193 (Alan R. Liss, Inc. 1989); Lewis and Dean, 1989 Proc. R. Soc. Lond. 236, 125-140 and 141-162; and, with respect to a model enzyme for nucleic acid components, Askew, et al., 1989 J. Am. Chem. Soc. 111, 1082-1090. Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are exemplified for application to drugs specific to particular proteins, they can be used to design of peptides and drugs that mimic P4 or the PsaA receptor.

In the screening methods disclosed, the cell used in the method can be any cell expressing a PsaA receptor, for example, pneumocytes, epithelial cells or endothelial cells. The cell can, alternatively, be an engineered cell that expresses a receptor mimic (e.g., a PsaA binding domain). In the method, the PsaA can be on a bacterial cell. Alternatively, in the method, the PsaA can be purified. The purified PsaA can be bound to a carrier surface such as a microsphere or similar surface.

Combinatorial chemistry includes but is not limited to all methods for isolating macromolecules that are capable of binding or mimicking either a small molecule or another macromolecule. Proteins, oligonucleotides, and sugars are examples of macromolecules. Screening sets of molecules for a desired activity whether based on small organic libraries, oligonucleotides, or antibodies is broadly referred to as combinatorial chemistry. Combinatorial techniques are particularly suited for defining binding interactions between molecules and for isolating molecules that have a specific binding activity, often called aptamers when the macromolecules are nucleic acids.

There are a number of methods for isolating proteins which either have specified activity or a modified activity. For example, phage display libraries have been used for a number of years.

A preferred method for isolating proteins that have a given function is described by Roberts and Szostak (Roberts R. W. and Szostak J. W. Proc. Natl. Acad. Sci. USA, 94(23)12997-302 (1997). This combinatorial chemistry method couples the functional power of proteins and the genetic power of nucleic acids. An RNA molecule is generated in which a puromycin molecule is covalently attached to the 3'-end of the RNA molecule. An in vitro translation of this modified RNA molecule causes the correct protein, encoded by the RNA to be translated. In addition, because of the attachment of the puromycin, a peptidyl acceptor which cannot be extended, the growing peptide chain is attached to the puromycin which is attached to the RNA. Thus, the protein molecule is attached to the genetic material that encodes it. Normal in vitro selection procedures can now be done to isolate functional peptides. Once the selection procedure for peptide function is complete traditional nucleic acid manipulation procedures are performed to amplify the nucleic acid that codes for the selected functional peptides. After amplification of the genetic material, new RNA is transcribed with puromycin at the 3'-end, new peptide is translated and another functional round of selection is performed. Thus, protein selection can be performed in an iterative manner just like nucleic acid selections. The peptide which is translated is controlled by the sequence of the RNA attached to the puromycin. This sequence can be anything from a random sequence engineered for optimum translation (i.e. no stop codons etc.) or it can be a degenerate sequence of a known RNA molecule to look for improved or altered function of a known peptide. The conditions for nucleic acid amplification and in vitro translation are well known to those of ordinary skill in the art and are preferably performed as in Roberts and Szostak (Roberts R. W. and Szostak J. W. Proc. Natl. Acad. Sci. USA, 94(23)12997-302 (1997)).

Another preferred method for combinatorial methods designed to isolate peptides is described in Cohen et al. (Cohen B. A., et al., Proc. Natl. Acad. Sci. USA 95(24): 14272-7 (1998)). This method utilizes and modifies two-hybrid technology. Yeast two hybrid systems are useful for the detection and analysis of protein:protein interactions. The two hybrid system, initially described in the yeast *Saccharomyces cerevisiae*, is a powerful molecular genetic technique for identifying new regulatory molecules, specific to the protein of interest (Fields and Song, Nature 340:245-6 (1989)). Cohen et al., modified this technology so that novel interactions between synthetic or engineered peptide sequences could be identified which bind a molecule of choice. The benefit of this type of technology is that the selection is done in an intracellular environment. The method utilizes a library of peptide molecules that attached to an acidic activation domain. A P4 peptide, for example SEQ ID NO:1 is attached to a DNA binding domain of a transcriptional activation protein, such as Gal 4. By performing the Two-hybrid technique on this type of system, molecules that bind P4 (e.g., receptors) are identified.

Using methodologies well known to those of skill in the art, in combination with various combinatorial libraries, one can isolate and characterize those, which bind to or interact with P4 or the PsaA receptor. The relative binding affinity of these compounds can be compared and optimum compounds identified using competitive binding studies, which are well known to those of skill in the art.

Techniques for making combinatorial libraries and screening combinatorial libraries to isolate molecules which bind a desired target are well known to those of skill in the art. Representative techniques and methods can be found in but are not limited to U.S. Pat. Nos. 5,084,824, 5,288,514, 5,449,754, 5,506,337, 5,539,083, 5,545,568, 5,556,762, 5,565,324, 5,565,332, 5,573,905, 5,618,825, 5,619,680, 5,627,210, 5,646,285, 5,663,046, 5,670,326, 5,677,195, 5,683,899, 5,688,696, 5,688,997, 5,698,685, 5,712,146, 5,721,099, 5,723,598, 5,741,713, 5,792,431, 5,807,683, 5,807,754, 5,821,130, 5,831,014, 5,834,195, 5,834,318, 5,834,588, 5,840,500, 5,847,150, 5,856,107, 5,856,496, 5,859,190, 5,864,010, 5,874,443, 5,877,214, 5,880,972, 5,886,126, 5,886,127, 5,891,737, 5,916,899, 5,919,955, 5,925,527, 5,939,268, 5,942,387, 5,945,070, 5,948,696, 5,958,702, 5,958,792, 5,962,337, 5,965,719, 5,972,719, 5,976,894, 5,980,704, 5,985,356, 5,999,086, 6,001,579, 6,004,617, 6,008,321, 6,017,768, 6,025,371, 6,030,917, 6,040,193, 6,045,671, 6,045,755, 6,060,596, and 6,061,636.

Combinatorial libraries can be made from a wide array of molecules using a number of different synthetic techniques. For example, libraries containing fused 2,4-pyrimidinediones (U.S. Pat. No. 6,025,371) dihydrobenzopyrans (U.S. Pat. Nos. 6,017,768 and 5,821,130), amide alcohols (U.S. Pat. No. 5,976,894), hydroxy-amino acid amides (U.S. Pat. No. 5,972,719) carbohydrates (U.S. Pat. No. 5,965,719), 1,4-benzodiazepin-2,5-diones (U.S. Pat. No. 5,962,337), cyclics (U.S. Pat. No. 5,958,792), biaryl amino acid amides (U.S. Pat. No. 5,948,696), thiophenes (U.S. Pat. No. 5,942,387), tricyclic Tetrahydroquinolines (U.S. Pat. No. 5,925,527), benzofurans (U.S. Pat. No. 5,919,955), isoquinolines (U.S. Pat. No. 5,916,899), hydantoin and thiohydantoin (U.S. Pat. No. 5,859,190), indoles (U.S. Pat. No. 5,856,496), imidazol-pyrido-indole and imidazol-pyrido-benzothiophenes (U.S. Pat. No. 5,856,107) substituted 2-methylene-2,3-dihydrothiazoles (U.S. Pat. No. 5,847,150), quinolines (U.S. Pat. No. 5,840,500), PNA (U.S. Pat. No. 5,831,014), containing tags (U.S. Pat. No. 5,721,099), polyketides (U.S. Pat. No. 5,712,146), morpholino-subunits U.S. Pat. Nos. 5,698,685 and 5,506,337), sulfamides (U.S. Pat. No. 5,618,825), and benzodiazepines (U.S. Pat. No. 5,288,514).

Diagnostic Methods

Diagnostic uses of the antibodies of the invention are suited for use in immunoassays in which they can be utilized in liquid phase or bound to a solid phase carrier. In addition, the monoclonal antibodies in these immunoassays can be detectably labeled in various ways. Examples of types of immunoassays which can utilize monoclonal antibodies of the invention are competitive and noncompetitive immunoassays in either a direct or indirect format. Examples of such immunoassays are the radioimmunoassay (RIA) and the sandwich (immunometric) assay. Detection of the antigens using the monoclonal antibodies of the invention can be done utilizing immunoassays which are run in either the forward, reverse, or simultaneous modes, including immunohistochemical assays on physiological samples.

The monoclonal antibodies of the invention can be bound to many different carriers and used to detect the presence of *S. pneumoniae* PsaA-specific antigens, for example a P4 peptide (e.g., SEQ ID NO:1). Examples of well-known carriers include glass, polystyrene, polypropylene, polyethylene, dextran, nylon, amylases, natural and modified celluloses, polyacrylamides, agaroses and magnetite. The nature of the carrier can be either soluble or insoluble for purposes of the invention. Those skilled in the art will know of other suitable carriers for binding monoclonal antibodies, or will be able to ascertain such, using routine experimentation.

There are many different labels and methods of labeling known to those of ordinary skill in the art as further described herein. Those of ordinary skill in the art will know of other suitable labels for binding to the monoclonal antibody, or will be able to ascertain such, using routine experimentation. Furthermore, the binding of these labels to the monoclonal antibody of the invention can be done using standard techniques common to those of ordinary skill in the art. Normally, a "sample" as used herein is a liquid such as urine, saliva, cerebrospinal fluid, blood, serum and the like, or a solid or semi-solid such as tissues, feces, and the like. Other possible examples of body fluids include nasal secretions, sputum, mucus and the like. Another technique which may also result in greater sensitivity consists of coupling the antibodies to low molecular weight haptens. These haptens can then be specifically detected by means of a second reaction. For example, it is common to use such haptens as biotin, which reacts with avidin, or dinitrophenyl, pyridoxal, and fluorescein, which can react with specific anti-hapten antibodies. As used in this invention, the term "epitope" is meant to include any determinant capable of specific interaction with the monoclonal antibodies of the invention. Epitopic determinants usually consist of chemically active surface groupings of molecules such as amino acids or sugar side chains and usually have specific three dimensional structural characteristics, as well as specific charge characteristics.

The present invention provides a method of detecting *S. pneumoniae* infection in a subject, comprising the steps of contacting an antibody-containing sample from the subject with a detectable amount of the P4 antigens of the present invention, under suitable reaction conditions, and detecting the reaction of the peptide and the antibody specifically reactive therewith, the reaction indicating the presence of *S. pneumoniae* or previous infection with *S. pneumoniae*. Detectable amounts of the present antigens can be determined empirically. The concentration of an individual antigen in a mixture can also be determined empirically.

One example of the method of detecting an organism or protein possessing the P4 antigen or variants is performed by contacting a fluid or tissue sample from the subject with an amount of a purified antibody specifically reactive with the antigen, and detecting the reaction of the ligand with the antigen. It is contemplated that the antigen will be on intact *S. pneumoniae* cells or *S. pneumoniae*-infected cells expressing the antigen, or will be fragments of the antigen. As contemplated herein, the antibody includes any ligand which binds the P4 antigen, for example, an intact antibody, a fragment of an antibody or another reagent that has reactivity with the antigen.

Enzyme immunoassays such as immunofluorescence assays (IFA), enzyme linked immunosorbent assays (ELISA) and immunoblotting can be readily adapted to accomplish the detection of the antibodies. An ELISA method effective for the detection of the antibodies can, for example, be as follows: (1) bind the antigen to a substrate; (2) contact the bound antigen with a fluid or tissue sample containing the antibody; (3) contact the above with a secondary antibody bound to a detectable moiety which is reactive with the bound antibody (e.g., horseradish peroxidase enzyme or alkaline phosphatase enzyme); (4) contact the above with the substrate for the enzyme; (5) contact the above with a color generating reagent under conditions that allow a color reaction to develop; (6) observe color change.

Another immunologic technique that can be useful in the detection of *S. pneumoniae* or previous *S. pneumoniae* infection utilizes monoclonal antibodies (MAbs) for detection of antibodies specifically reactive with P4 antigens. Briefly, sera from the subject is reacted with the antigen bound to a substrate (e.g. an ELISA 96-well plate). Excess sera is thoroughly washed away. A labeled (enzyme-linked, fluorescent, radioactive, etc.) monoclonal antibody is then reacted with the previously reacted antigen-serum antibody complex. The amount of inhibition of monoclonal antibody binding is measured relative to a control (no patient serum antibody). The degree of monoclonal antibody inhibition is a very specific test for a particular variety or strain since it is based on monoclonal antibody binding specificity. MAbs can also be used for detection directly in cells by IFA.

A micro-agglutination test can also be used to detect the presence of anti-P4 antibodies in a subject. Briefly, latex beads, red blood cells or other agglutinable particles are coated with the antigen and mixed with a sample from the subject, such that antibodies in the tissue or body fluids that are specifically reactive with the antigen crosslink with the antigen, causing agglutination. The agglutinated antigen-antibody complexes form a precipitate, visible with the naked eye or by spectrophotometer. In a modification of the above test, antibodies specifically reactive with the antigen can be bound to the beads and antigen in the tissue or body fluid thereby detected.

In addition, as in a typical sandwich assay, the antibody can be bound to a substrate and reacted with the antigen. Thereafter, a secondary labeled antibody is bound to epitopes not recognized by the first antibody and the secondary antibody is detected. Since the present invention provides P4 antigens for the detection of *S. pneumoniae* or previous *S. pneumoniae* infection other serological methods such as flow cytometry and immunoprecipitation can also be used as detection methods.

In the diagnostic methods taught herein, the antigen can be bound to a substrate and contacted by a fluid sample such as blood, serum, urine or saliva. This sample can be taken directly from the patient or in a partially purified form. In this manner, antibodies specific for the antigen (the primary antibody) will specifically react with the bound antigen. Thereafter, a secondary antibody bound to, or labeled with, a detectable moiety can be added to enhance the detection of the primary antibody. Generally, the secondary antibody or other ligand which is reactive, either specifically with a different epitope of the antigen or nonspecifically with the ligand or reacted antibody, will be selected for its ability to react with multiple sites on the primary antibody. Thus, for example, several molecules of the secondary antibody can react with each primary antibody, making the primary antibody more detectable.

The diagnostic kit of the present invention can be used to detect the presence of a primary antibody specifically reactive with one or more of the antigenic peptides of PsaA. The kit can include the P4 or PsaA antigen(s) of the present invention bound to a substrate, a secondary antibody reactive with the antibody specifically reactive with the selected antigens and a reagent for detecting a reaction of the secondary antibody with the primary antibody. Such a kit can be an ELISA kit and can comprise the substrate, antigen, primary and secondary antibodies when appropriate, and any other necessary reagents such as detectable moieties, enzyme substrates and color reagents as described above. The diagnostic kit can, alternatively, be an immunoblot kit generally comprising the components and reagents described herein.

The diagnostic kit of the present invention can be used to detect the presence of immunogenic epitopes of PsaA and P4 antigens as well as PsaA receptors. The kit can include selected antibodies bound to a substrate, a secondary antibody reactive with the antigen and a reagent for detecting a reaction of the secondary antibody with the antigen, wherein selected antibodies bound to the substrate may be immunoreactive with PsaA antigens or PsaA receptors. Such a kit can be an ELISA kit and can comprise the substrate, primary and secondary antibodies when appropriate, and any other necessary reagents such as detectable moieties, enzyme substrates and color reagents as described above. The diagnostic kit can, alternatively, be an immunoblot kit generally comprising the components and reagents described herein. The kit can be an array kit, where PsaA or a P4 peptide is one of the antigenic targets.

The particular reagents and other components included in the diagnostic kits of the present invention can be selected from those available in the art in accord with the specific diagnostic method practiced in the kit. Such kits can be used to detect the antigen in tissue and fluid samples from a subject.

Sequences

```
LFVESSVRRPMKTVSQDTNIPIYAQIF                     (P4; SEQ ID NO: 1)

VPSLFVDSSVDDRPVSQDTNIPIYAQIFTDSIA                  (SEQ ID NO: 2)

TVSRVPWTAWAFHGY                                 (P1; SEQ ID NO: 3)

RSYQHDLRAYGFWRL                                 (P2; SEQ ID NO: 4)

LVRRFVHRRPHVE-SQ                                (P3; SEQ ID NO: 5)

X1X2X3LFVESSVKRRPMKTVSQDTNIPIYAQIFX4X5X6            (SEQ ID NO: 6)

LFVESSVDDRPMKTVSKDTNIPIYAKIF                       (SEQ ID NO: 7)

LFVESSVDDRPMKTVSKDTNIPIYSTIF                       (SEQ ID NO: 8)

LFVESSVDDRKTVSKDTNIPIHAKIF                         (SEQ ID NO: 9)

LFVESSVDDRPMETVSKDSGIPIYAEIF                      (SEQ ID NO: 10)

LFVESSVDRRPMETVSKDSGIPIYSEIF                      (SEQ ID NO: 11)

LFVESSVDKRPMKSVSRESGIPIYAEIF                      (SEQ ID NO: 12)

LFVESSVDDRPMKTISKETGISIYSKIF                      (SEQ ID NO: 13)

LFVETSVDRRSMETVSKETNVPIAGTIF                      (SEQ ID NO: 14)

LFVETSVDPRSMESVSKETGVPIFAKIF                      (SEQ ID NO: 15)

QDTNIPIYAQI                                       (SEQ ID NO: 16)

LFVESSVKRRPMKTVS                                  (SEQ ID NO: 17)
where X1 is H, V, I or L
where X2 is H, P or G
where X3 is H, S or T
```
-continued
```
where X4 is H, T or S
where X5 is H or D, and
where X6 is H, S or T
```

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in C or is at ambient temperature, and pressure is at or near atmospheric.

Example 1

*S. pneumoniae* PsaA and Human Nasopharyngeal Epithelial Cells—Evaluation of Adhesin-Receptor Interaction This example evaluates the adherence capacity of this protein to human nasopharyngeal (NP) epithelial cells (Detroit 562). The functional epitope is localized to a peptide sequence (aa 251-278 of GenBank accession no. gi|7920462|gb|AAF70667.1) including strand 7, α-helix 8, and strand 8 of PsaA. This peptide sequence (P4) was found to efficiently bind to Detroit 562 cells and to inhibit ($\geq$95%) the binding of PsaA protein.

Relevant Epitopes

Previously, three peptides (P1, P2 & P3) were identified by phage display (Srivastava, et al. 2000; and U.S. patent application Ser. No. 09/623,038, incorporated herein by reference for the teaching of these peptides). Antibodies to the peptides reduce colonization in mice immunized with the peptides (Johnson, et al. 2002). These peptides are functionally reactive but not identical to the PsaA sequence. Their amino acid sequences are as follows:

```
P1:    T-V-S-R-V-P-W-T-A-W-A-F-H-G-Y
       (SEQ ID NO: 3)

P2:    R-S-Y-Q-H-D-L-R-A-Y-G-F-W-R-L
       (SEQ ID NO: 4)

P3:    L-V-R-R-F-V-H-H-R-P-H-V-E-S-Q
       (SEQ ID NO: 5)
```

Peptide P1 was found to contain a functional epitope for the adherence of PsaA to NP cells (See Example 4).

Peptide P4 is 96.1% similar to the PsaA sequence thought to contain the functional epitope found in P1. This variability is due to the two DD residues of the wild-type sequence that were changed to KR in the P4 sequence to facilitate binding to fluorospheres. SEQ ID NO: 2 shows these two amino acid substitutions and a further difference from SEQ ID NO: 1.

```
P4:    L-F-V-E-S-S-V-K-R-R-P-M-K-T-V-S-Q-D-T-N-I-P-Y-
       A-Q-I-F (SEQ ID NO: 1)
```

Methods:

Carboxylate-modified fluorospheres (Molecular Probes™, 1 mm in diameter) coated with either recombinant PsaA (rPsaA) or PsaA synthetic peptide (P4) were evaluated for their adherence to Detroit 562 NP cells. Four different batches of PsaA beads were generated by varying the concentration of the protein solution used to coat the beads (0.9 mg/ml, 0.53 mg/ml, 5.3 µg/ml and 0.53 µg/ml). P4 and Glycine control beads were generated by using a peptide solution (0.9 mg/ml). Protein concentrations were confirmed by the Bradford test (Sigma). PsaA and peptide beads were compared at similar inocula (1640±210 beads per well) in adherence and adherence competition assays (measured as mean fluorescent units (FU±SE)).

Results:

rPsaA-Coated Beads:

0.9 mg/ml PsaA beads showed the highest adherence (47,875 FU±1385), followed by the 0.53 mg/ml batch of PsaA beads (16,748 FU±205), and the 5.3 µg/ml PsaA beads (12,788 FU±265). 0.53 µg/ml PsaA beads showed the least adherence (5,892 FU±316).

P4-Coated Beads:

Adherence was 19,340 FU±508; Glycine-coated control beads adherence was 2,799 FU±137. Competition of P4-coated beads with 5 µg, 10 µg and 20 µg of P4 peptide suspended in solution resulted in 89%, 88% and 89% reduction in FU, respectively. Competition of PsaA-coated beads with 5 µg, 100 µg and 20 µg of P4 peptide resulted in 23%, 68% and 95% reduction in FU.

In summary, PsaA is a Pnc adhesin that binds to human NP epithelial cells. PsaA bead adherence is PsaA protein concentration dependent. P4 peptide contains a functional epitope for PsaA adherence. By providing the functional epitope mediating bacterial adherence and an isolated peptide comprising that epitope, an improved Pneumococcal vaccine is provided. The epitope-containing peptide is also useful for the specific measurement and identification of functional antibodies. This, permits the production of antibodies that treat Pneumococcal disease. The provided epitope peptide is a basis for a S. pneumoniae diagnostic assay.

TABLE 3

Competitive Inhibitions

| Competitor P4 peptide (µg/well) | Percent reduction in adherence according to bead target | |
|---|---|---|
| | rPsaA-coated (0.9 mg/ml batch) | P4-coated |
| 5.0 | 18.5 | 89.4 |
| 10 | 57.6 | 87.6 |
| 20 | 95.9 | 88.9 |

Table 3 shows percent inhibition of PsaA-bead and P4-bead adherence as compared to control wells in the absence of inhibitor (P4 peptide). All bead types were added at the same concentration to the assay wells (~1,640 beads in 20 µl of buffer).

Example 2

Rabbit Immunization with Multi Antigenic Peptides (MAP) of P4

The MAPs consist of two arms, each consisting of SEQ ID NO:1 linked via lys or nle-lys to a resin.

| Animals: | Female rabbits, age 7 months |
|---|---|
| Immunization schedule: | Dose - 1; Day 0 |
| | Dose - 2; Day 21 |
| | Dose - 3; Day 35 |
| Dosage: | 5 to 25 µg per animal |
| Schedule of bleeds: | 1) Pre-immunization bleed; Day 0 |
| | 2) Post immunization bleed - 1; Day 28 |
| | 3) Final bleed (bleed - 2); Day 42 |

Assessment of Serum Samples:

1) Inhibition of adherence of P4 coated fluorescent beads to Detroit 562 cells (in vitro; tissue culture) to detect the presence of anti P4 antibodies in serum.
2) Inhibition of adherence of PsaA coated fluorescent beads to Detroit 562 cells (in vitro; tissue culture) to detect the presence of anti PsaA antibodies in the serum.
3) Inhibition of adherence of Pneumococci (Pnc) to Detroit 562 cells (in vitro; tissue culture) to detect the presence of anti Pnc antibodies in serum.

Immunization with P4E—Analyses of Rabbit Sera for Anti P4 and Anti Pneumococcal (Pnc) Antibody:

Animal 465

TABLE 4

Anti P4 and anti Pnc activity in serum samples

| | % inhibition of adherence (% IA; Mean of triplicates) | | | | | |
|---|---|---|---|---|---|---|
| | Anti P4 activity | | | Anti Pneumococcal activity | | |
| Serum Dilution | Pre-bleed | Bleed #1 | Bleed #2 | Pre-bleed* | Bleed #1 | Bleed #2 |
| 1:10 | 0 | 39 | 43 | 5 | 0 |
| 1:100 | 0 | 32 | 8 | 25 | 4 |
| 1:1000 | 0 | 33 | 9 | 24 | 5 |
| 1:8000 | 0 | 6 | 5 | 23 | 13 |
| 1:16000 | 0 | 12 | 7 | 25 | 14 |
| 1:32000 | 0 | 5 | 9 | 5 | 14 |
| 1:64000 | 0 | 22 | 6 | * | * |
| 1:128000 | 0 | 10 | 5 | * | * |
| 1:256000 | 0 | 5 | 0 | * | * |
| 1:512000 | 0 | 5 | 6 | * | * |

% IA values that are above the assay variability (20%) are considered for analysis.
* = Not tested.

Animal 467

TABLE 5

Anti P4 and anti Pnc activity in serum samples

| | % inhibition of adherence (% IA; mean of triplicates) | | | | | |
|---|---|---|---|---|---|---|
| | Anti P4 activity | | | Anti Pneumococcal activity | | |
| Serum Dilution | Pre-bleed | Bleed #1 | Bleed #2 | Pre-bleed | Bleed #1 | Bleed #2 |
| 1:10 | 0 | 46 | 48 | 0 | 38 | 21 |
| 1:100 | 0 | 29 | 28 | 8 | 55 | 21 |
| 1:1000 | 0 | 41 | 12 | 4 | 38 | 39 |
| 1:8000 | 0 | 9 | 4 | 6 | 34 | 21 |
| 1:16000 | 0 | 15 | 1 | 0 | 27 | 41 |
| 1:32000 | 0 | 17 | 5 | * | 22 | 16 |
| 1:64000 | 0 | 21 | 3 | * | * | * |
| 1:128000 | 0 | 15 | 9 | * | * | * |
| 1:256000 | 0 | 7 | 3 | * | * | * |
| 1:512000 | 0 | 7 | 3 | * | * | * |

% IA values that are above the assay variability (20%) are considered for analysis.
* = Not tested Immunization with P4E2—Analyses of Rabbit Sera for Anti P4 and Anti Pneumococcal Antibody:

Animal 469

TABLE 6

Anti P4 and anti Pnc activity in serum samples

% inhibition of adherence
(% IA; mean of triplicates)

| Serum Dilution | Anti P4 activity | | | Anti Pneumococcal activity | | |
|---|---|---|---|---|---|---|
| | Pre-bleed | Bleed #1 | Bleed #2 | Pre-bleed | Bleed #1 | Bleed #2 |
| 1:10 | 0 | 50 | 74 | 0 | 5 | 17 |
| 1:100 | 0 | 0 | 0 | 0 | 21 | 30 |
| 1:1000 | 0 | 0 | 4 | 0 | 22 | 33 |
| 1:8000 | 0 | 0 | 1 | 0 | 19 | 22 |
| 1:16000 | 0 | 0 | 0 | 0 | 15 | 18 |
| 1:32000 | 0 | 0 | 0 | 0 | 0 | 1 |
| 1:64000 | 0 | 0 | 2 | 0 | * | * |
| 1:128000 | 0 | 0 | 4 | 0 | * | * |
| 1:256000 | 0 | 0 | 4 | 0 | * | * |
| 1:512000 | 0 | 0 | 0 | 0 | * | * |

% IA values that are above the assay variability (20%) are considered for analysis.
* = Not tested Animal 471

TABLE 7

Anti P4 and anti Pnc activity in serum samples

% inhibition of adherence
(% IA; mean of triplicates)

| Serum Dilution | Anti P4 activity | | | Anti Pneumococcal activity | | |
|---|---|---|---|---|---|---|
| | Pre-bleed | Bleed #1 | Bleed #2 | Pre-bleed | Bleed #1 | Bleed #2 |
| 1:10 | 0 | 56 | 75 | | 38 | 3 |
| 1:100 | 0 | 0 | 3 | | 3 | 0 |
| 1:1000 | 0 | 0 | 1 | | 23 | 20 |
| 1:8000 | 0 | 0 | 2 | | 21 | 16 |
| 1:16000 | 0 | 0 | 0 | | 2 | 12 |
| 1:32000 | 0 | 0 | 0 | | 0 | 23 |
| 1:64000 | 0 | 0 | 4 | | * | * |
| 1:128000 | 0 | 0 | 0 | | * | * |
| 1:256000 | 0 | 0 | 5 | | * | * |
| 1:512000 | 0 | 0 | 0 | | * | * |

% IA values that are above the assay variability (20%) are considered for analysis.
* = Not tested

Example 3

Mouse Immunization with P4 and PsaA

TABLE 8

Mice serum - anti P4/PsaA data

Anti P4/PsaA activity
(% IA of P4/PsaA beads)

| Serum Dilution Factor | P4 | | | PsaA | | |
|---|---|---|---|---|---|---|
| | Pre | 7th day | 11th day | Pre | 7th day | 11th day |
| 8 | 85 | 81 | 95 | 71 | 84 | 79 |
| 16 | 46 | 40 | 44 | 30 | 47 | 37 |
| 32 | 0 | 31 | 45 | 0 | 42 | 34 |
| 64 | 0 | 0 | 4 | 0 | 0 | 11 |
| 128 | 0 | 0 | 0 | 0 | 0 | 1 |
| 256 | 0 | 0 | 0 | 0 | 0 | 0 |
| 512 | 0 | 0 | 0 | 0 | 0 | 0 |
| 1024 | 0 | 0 | 0 | 0 | 0 | 0 |
| 2048 | 0 | 0 | 0 | 0 | 0 | 4 |
| 4096 | 0 | 0 | 0 | 0 | 0 | 18 |

Up to 45% inhibition of adherence was detected in sera (1:32 dilution) from mice immunized with P4 peptide, whereas no inhibition of adherence was detected in the pre-immunization sera.

Example 4

Adherence of Pneumococcal Surface Adhesin A (PsaA)-Coated Particles to Human Nasopharyngeal Epithelial Cells for the Evaluation of Anti-PsaA Functional Antibodies Materials and Methods
Preparation of Detroit 562 Cell Monolayers Nasopharyngeal human carcinoma epithelial cells (Detroit 562 cells) were obtained from the American Type Culture Collection, Manassas, Va. (CCL138, ATCC, Rockville, Md.). Stock cultures were seeded at $1 \times 10^5$ cells/mL in T-75 cm$^2$ tissue culture bottles (Corning Costar Co., Cambridge, Mass.). The growth medium used was minimal essential medium with Earle's salts (EMEM), without L-glutamine (Life Technologies, Grand Island, N.Y.), and supplemented with 10% fetal calf serum (Hyclone, Logan, Utah). Cells were grown at 37° C. and under a 5% $CO_2$ atmosphere for 7 days. Monolayers for adherence assays were seeded with 200 µL/well of a $2 \times 10^5$ cells/mL suspension in 96-well tissue culture treated plates (Corning Costar Co., Corning, N.Y.) and allowed to reach confluent growth for 6 days as previously described (Romero-Steiner). Monolayers (96-well plates) could be used at 6 or 7 days without affecting the adherence of the coated particles.

Source of PsaA Protein and Peptides

Purified recombinant PsaA (multiple lots ranging from 1.8 to 2.8 mg/ml) was kindly donated by Aventis-Pasteur, Toronto, Ontario, Canada. In addition, three synthetic peptides were used with sequences identified by phage display (Srivastrava). These sequences were used in animal immunogenicity and protection studies (Johnson). These peptides are functionally reactive but not identical to the PsaA protein sequence (FIG. 4.). The peptide sequences were as follows: P1=T-V-S-R-V-P-W-T-A-W-A-F-H-G-Y (SEQ ID NO: 3, MW=1,796.9 daltons), P2=R-S-Y-Q-H-D-L-R-A-Y-G-F-W-

R-L (SEQ ID NO: 4, MW=1,512.6 daltons), and P3=L-V-R-R-F-V-H-R-R-P-H-V-E-S-Q (SEQ ID NO: 5, MW=1,916.2 daltons). Each peptide was synthesized as a branched peptide using a two amino acid linker (lysine and nor-leucine) at the carboxyl-terminus as previously described by Johnson et al. (Johnson). A fourth peptide (P4) was derived by comparison of the P1 and P3 peptide sequences to PsaA. P4 was not branched and it contained the homologous amino acid sequence of PsaA (MW=3,254.8 daltons, amino acid residues 251 to 278; L-F-V-E-S-S-V-K-R-R-P-M-K-T-V-S-Q-D-T-N-I-P-I-Y-A-Q-I-F; SEQ ID NO: 1), where P1 and P3 were mapped. Both, rPsaA (MW 34,079 daltons) and the synthetic peptides were non-lipidated. The two amino acids given in bold are different from the PsaA sequence given in gi|7920462|gb|AAF70667.1, in order to generate a peptide with a net positive charge for binding to the carboxylate-modified fluospheres. These conservative substitutions were made in an amino acid region between strand 7 and helix 8 of the protein to minimize any effects on functional domains (FIG. 4).

Labeling of Carboxylate-Modified Fluospheres with rPsaA or Peptides

Recombinant PsaA protein or synthetic peptides were covalently bound to carboxylate-modified FluoSpheres (Molecular Probes, Eugene, Oreg.) (505/515 nm range, yellow, 1 μm in diameter). All peptides had a positive net charge at pH 6.0, which facilitated the binding to carboxylate-modified fluospheres. The 2% fluosphere stock was vortexed for 2 minutes at full speed. A 250-μl aliquot was sonicated for 5 minutes to break clumps. The sonicated fluospheres were washed 3 times by centrifugation at 10,000 rpm for 10 minutes in 250 μl MES buffer, pH 6.0 (Molecular Probes). The negative charge in the carboxylate-modified fluospheres was activated by adding 50 μl of EDAC solution (100 mg/ml, Molecular Probes) to the washed fluospheres resuspended in 200 μl MES. The fluospheres were incubated for 30 minutes RT with gentle rotation. A 250-μl volume of rPsaA (1 mg/ml) or peptide (2 mg/ml) resuspended in MES buffer was added to each fluosphere pellet. Suboptimal concentrations of rPsaA (900, 530, 5.3 and 0.53 μg/ml) were also used to generate partially coated fluospheres. Peptides were dissolved as 1 mg in 50 μl of 10% acetic acid followed by addition of 450 μl of MES buffer, pH 6.0. The 500-μl fluosphere suspension was incubated in the dark over night at room temperature with horizontal rotation (150 rpm). The remaining reactive sites were blocked by addition of a 50-μl volume of 1 M solution of glycine, followed by a-30-minute incubation at room temperature with horizontal rotation. The fluosphere suspension was then washed with 500 μl PBS, 50 mM, pH 7.2-7.4 three times by centrifugation at 10,000 rpm for 10 minutes. The first supernatant of the first wash was saved for protein determinations using the microtiter microdilution method of Bradford (Bio-Rad Laboratories, Calif.). The labeled fluosphere pellet was resuspended in 500 μl of PBS, 50 mM, pH 7.2-7.4. Labeled fluospheres were stored in the dark in 100-μl aliquots at 4° C. for up to 4 months. The peptides were stored in powder form at 4° C. under Dryerite desiccant. The resuspended peptides were stored at 4° C. for 6 weeks and for long term storage at −70° C. Fluospheres were counted by limiting dilution using a fluorometer (FLX-600, BioTek) with 485/520 nm excitation/emission wavelength and comparison to a calibration curve previously generated against hemacytometer counts.

Adherence of rPsaA or Peptide-Coated Fluospheres to Detroit 562 Cells

Confluent monolayers of Detroit 562 cells grown in 96-well tissue culture plates for 6 days were washed once with 130 μl/well of PBS buffer+0.5% BSA (Sigma cat #A2153, Fraction V purified by alcohol precipitation). The entire outer perimeter of the microtiter plate was not used for adherence assays due to edge effect and lack of confluent growth in these wells. An 80-μl volume per well of PBS buffer+1% BSA and 20 μl per well of diluted fluosphere suspension (to yield ~3100±500 fluospheres in a 20-μl volume) were added to the washed monolayers. The diluted fluosphere suspension was sonicated for 3 minutes prior to addition to the center of the wells. Blank wells (column 11) did not contain fluospheres. The sides of the plates were then tapped gently to mix. The plate was allowed to incubate for 2 hours at 37° C., 5% $CO_2$. Following incubation, plates were washed 5 times with 130 μL/well of PBS+0.5% BSA. The liquid was removed after each wash with a multi-channel aspirator (Costar) and moderate vacuum. The plate was allowed to dry before reading in the fluorometer (485/520 nm). The file was exported as a text format into a spreadsheet (Excel, Windows 2000) to calculate the mean adherence and standard error (SE).

Competitive Inhibitions

Homologous competitive inhibitions with 0.5 to 10 μg per well of rPsaA protein or 5 to 20 μg per well of each peptide were performed to determine the specificity of the adherence for rPsaA-coated fluospheres or for each of the three peptide-coated fluospheres. Heterologous competitive inhibitions with each peptide (10 μg per well) were performed to determine which peptide blocked the adherence of whole PsaA-coated fluospheres to the Detroit 562 cells. Absorption of PsaA-specific antibodies was performed by incubation (2 hours at ambient room temperature with rotation, 100 rpm) of 500 μl (1:8 dilution) of the serum 7051 with nitrocellulose strips (2.5×0.5 cm), previously impregnated with rPsaA protein (1.8 mg/ml) and allowed to dry at 37° C. for 1 hour. Strips were replaced every 2 hours for a total of 3 changes. All antibody absorptions were performed in PBS (10 mM, pH 7.2) supplemented with 1% (weight/volume) BSA as a nonspecific blocker. Immunoglobulin G (IgG) concentrations (μg/ml) were measured as previously described (Tharpe, Romero-Steiner) after each absorption step to monitor the decline of anti-PsaA antibodies.

Serum Inhibition of Adherence Assays

Serum inhibition of adherence assays were performed as previously described for the inhibition of pneumococcal adherence (Romero-Steiner). Two buffer solutions were found suitable for this type of assay: solution 1 (EMEM medium—Hanks buffered saline with Ca++ and Mg++ supplemented with 0.2% BSA) as previously reported (Romero-Steiner) or solution 2 (PBS 10 mM, pH7.2-7.4 supplemented with 1% BSA and 0.5% BSA for washes) as described below. Use of one buffer solution in preference to the other depended on availability of BSA (Sigma cat #A2153). Alternative preparations of BSA were evaluated but were not found suitable for this assay due to toxicity to the cell monolayer. Briefly, confluent monolayers of Detroit 562 cells were washed once with 130 μl/well of PBS buffer+0.5% BSA. A 45 μl volume of PBS buffer+1% BSA was added to each well and the plate was incubated while preparing serum dilutions in a replicate plate (U-bottom Costar). Serum dilutions in the replica plate could be performed in a 2-fold or 3-fold dilution scheme. For the 2-fold dilution scheme, a 10 μl volume of test or control serum was added to the first row of wells (B2-B11) already containing 70 μl of PBS+1% BSA. A 40 μl volume of PBS+1% BSA was added to the remainder of the wells including the outer perimeter. The sera from row B was serially diluted into rows C-F with a multichannel pipetor set at 40 μl (2-fold). The last 40l was discarded into the waste.

Serum was not added to the adherence control wells (row G or column 11). A 20 μl volume of the optimal fluosphere dilution (usually 1:100 or 1:150, containing ~3,100 fluospheres) was added to each well, including serum-free controls. The fluosphere suspension was sonicated for 3 minutes prior to addition to the center of the wells to generate a single fluosphere suspension. The microtiter plate was mixed by tapping the sides gently and incubated for 15 minutes at 37° C., 5% $CO_2$. At the end of the incubation period, 55 μl/well was replica plated into the microtiter plate containing the washed monolayers containing 45 μl of PBS+1% BSA. The final well volume was always adjusted to 100-μl volume regardless of the serum dilution scheme used (2-fold or 3-fold) to control the reproducibility of fluosphere adherence The plate was mixed by tapping the sides gently and incubated for 2 hours at 37° C., 5% $CO_2$. Following incubation, plates were washed 5 times with 130 μl/well of PBS+0.5% BSA. The plates were allowed to dry before reading in a fluorometer (BioTek, FLX 800) at 485 nm for excitation and emission at 520 nm. The percent inhibition of adherence (IA) was calculated as compared to adherence controls. The following formula was used: % IA=100-(test well FU×100)/controls mean FU.

Results
Adherence of rPsaA and Peptide-Coated Fluospheres

Figure 5:
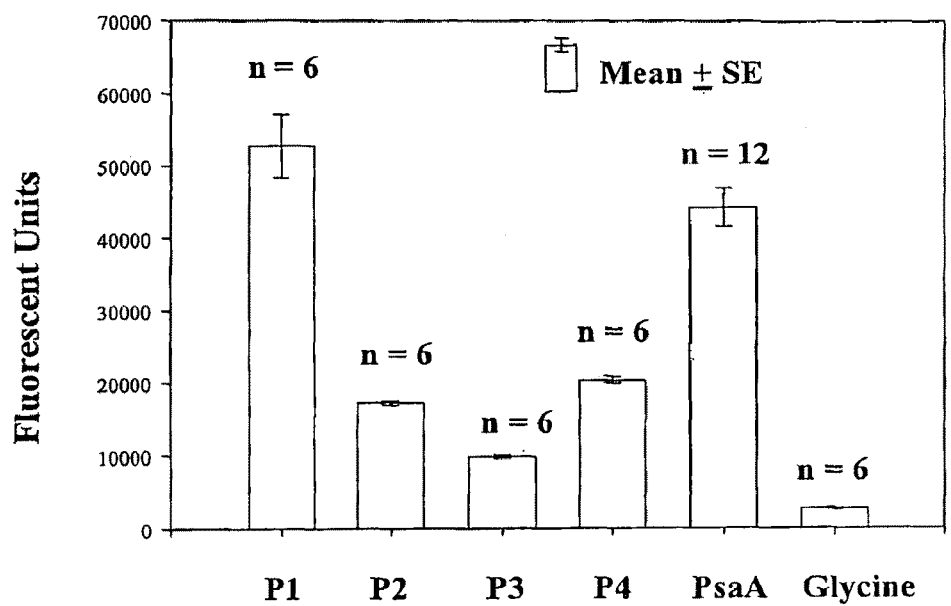
FIG. 5 shows mean adherence of P1-, P2-, P3-, P4-, and rPsaA-coated fluorospheres to Detroit 562 cells (mean FU±SE) when 3,100±500 fluorospheres were added per well. Control fluorospheres were coated with glycine to block any reactive carboxyl groups.
Figure 6:
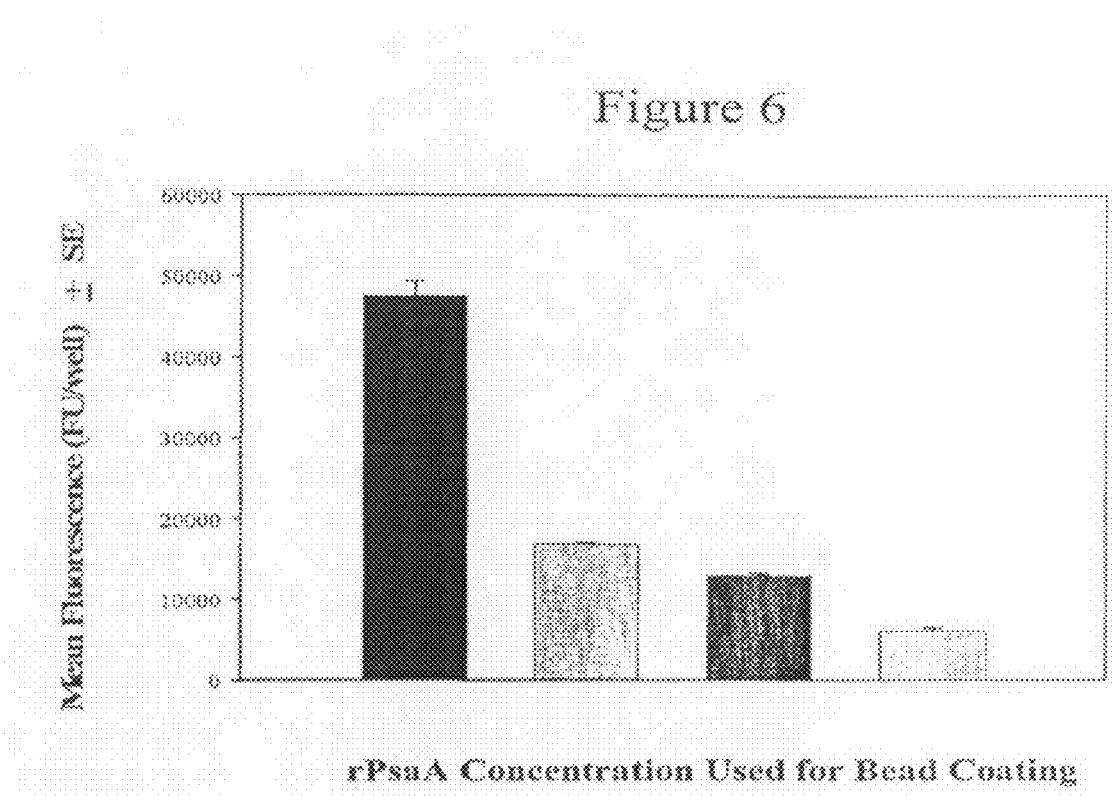
FIG. 6 shows adherence to Detroit 562 nasopharyngeal cells of fluorospheres coated with various rPsaA concentrations (900, 530, 5.3 and 0.53 µg/ml). The adherence signal is given as the mean FU±SE when 1,640±210 fluorospheres were added per well. Adherence of rPsaA fluospheres coated with 1 mg/ml of rPsaA is shown in FIG. 2A.

The relative adherence of rPsaA or peptide-coated fluospheres to Detroit 562 cells is given in FIG. 5. P1-coated fluospheres showed the most adherence to NP cells with mean FU±SE of 52,684±4,354, followed by rPsaA-coated fluospheres (mean FU=44,195±2,648), and P4-coated fluospheres (mean FU=20,317±448). P2- and P3-coated fluospheres showed the least adherence with mean FU=17,195±1,044 and 9,780±228, respectively. The number of coated fluospheres used to perform the assay was directly proportional with the FU signal observed after a 2 hour incubation period. Each batch of fluospheres generated was tested at different dilutions (usually 1:50, 1:100 and 1:200) to confirm the differential binding as the coated particles were diluted. Usually, rPsaA-P1- and P4-coated fluospheres at a 1:50 dilution gave an overflow signal (more than 100,000 FU). Most coated particles were used at dilutions between 1:100 and 1:200 to obtain a signal of 20,000 to 50,000 FU. Higher dilutions often resulted in signals of 10,000 FU or less. Adherence of rPsaA-coated fluospheres was also dependent on the amount of rPsaA used to coat the fluospheres (FIG. 6). The adherence of rPsaA fluospheres to the monolayer surface is shown in FIG. 3. This adherence increased with the incubation time. Mean adherence signal (n=6) for rPsaA coated fluospheres (2600 fluospheres/well) was 2,315 FU after a 20 min incubation and increased linearly to 17,498 FU after a 180 min incubation. Adherence started to plateau after a-140 min incubation (16,597 FU). Background signals in monolayer wells with no fluospheres added were 1,000±150. Adherence assays were performed in the presence of 1% BSA to block non-specific adherence to the monolayer. Yields of coated fluospheres varied slightly from batch to batch with a range between 1.3 and 1.8×10$^7$ fluospheres/ml and an estimated 0.5 pg of PsaA protein per fluosphere when the optimal concentration of rPsaA (1 mg/ml) was used for coating. Fluospheres were capable of adhering for up to 2 months after labeling with no difference in the binding capacity. For example, rPsaA-coated fluospheres (batch 6, dilution 1:100 yielding 2,600 fluospheres in a 20-μl volume) had a mean adherence and % CV at day 1 of 30,105 FU (18.5%) and at day 60 the mean adherence was 30,595 FU (6%).

Specificity of the Adherence

Figure 7:
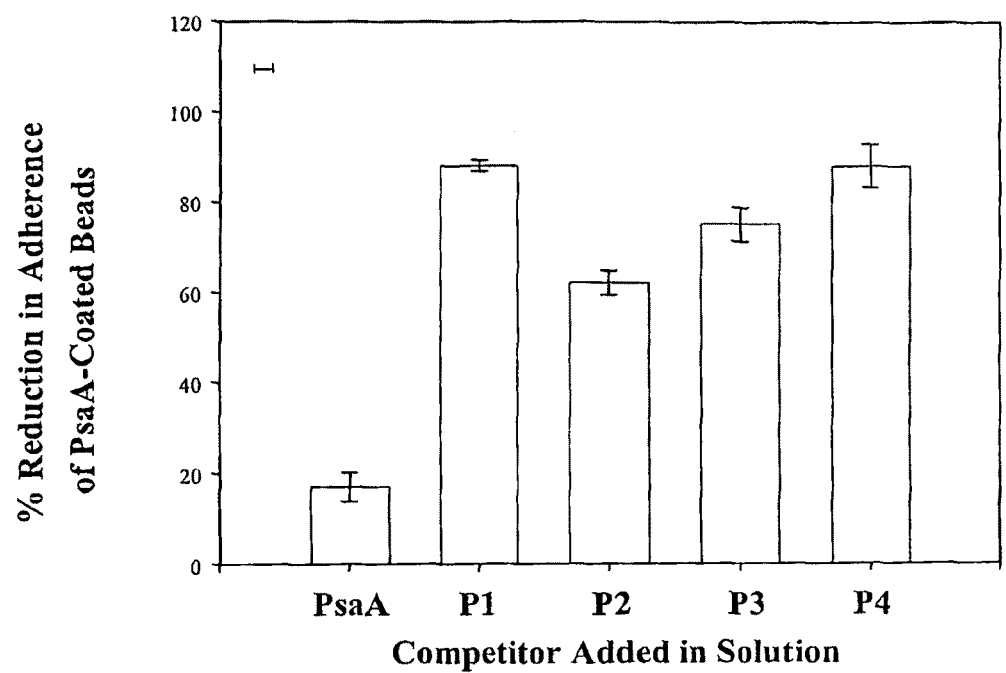
FIG. 7 shows competitive inhibition of adherence of rPsaA-coated fluospheres by addition of peptide (10 µg/well, 3 to $5 \times 10^{-2}$ mM) P1, P2, P3, P4, or 3 µg/well ($9 \times 10^{-4}$ mM) of rPsaA protein. Additional concentrations of rPsaA [range=0.125 to 10.0 µg/well (0.4 to $29.7 \times 10^{-4}$ mM)] did not result in any further reduction of adherence of rPsaA-coated fluospheres. Although not shown, we observed a 95.9% reduction of rPsaA coated fluosphere adherence when using 20 µg/well ($6.2 \times 10^{-2}$ mM) of P4 homologous peptide in the inhibition reaction. Mean (bars) and SD (whiskers) represent the average percent reduction obtained in 3 separate assays using multiple concentrations of PsaA fluospheres (225 to 7,200 fluospheres per well) with signals ranging between 5,500 to 100,000 FU for peptide heterologous inhibitions and between 5,500 and 23,000 FU for PsaA homologous inhibitions.

Table 9 shows the specificity of adherence of rPsaA- or peptide-coated fluospheres to Detroit 562 cells under homologous competition conditions with multiple concentrations of rPsaA or peptides added. Although increasing concentrations (0.5 to 10 μg/well) of rPsaA were added, we were unable to significantly reduce the adherence of rPsaA fluospheres with the whole recombinant protein. Addition of 10 μg/well (100 μg/ml) of P1, P2, P3, or P4 to their homologous peptide-coated fluosphere adherence reactions resulted in a 60.9%, 20.5%, 5.2%, and 87.6% reduction in adherence, respectively. Higher concentrations of P3 peptide (20 μg/well) yielded a 44.2% reduction in P3 adherence. P2 adherence could be reduced to 43.1% with lower concentrations of P2 peptide (5 μg/well). Heterologous competitions with each of the four peptides (10 μg/well) P1, P2, P3 inhibited 88.1%, 62.2%, 75.2%, and 57.6% of rPsaA-fluosphere adherence, respectively, as shown in FIG. 7. Heterologous competition with 20 μg/well of P4, yielded a 95.9% inhibition of rPsaA-fluosphere adherence. There was no additive effect in the reduction of PsaA adherence by the addition of peptides P1, P2 and P3 in the same reaction mixture.

TABLE 9

Percent reduction in adherence of rPsaA- and peptide-coated fluospheres to Detroit 562 cells following homologous competitive inhibition with rPsaA or each of the peptides.

| Homologous competitor (μg/well)[a] | rPsaA-coated | Peptides derived from phage display | | | Homologous P4-coated |
|---|---|---|---|---|---|
| | | P1-coated | P2-coated | P3-coated | |
| 0 | 0 | 0 | 0 | 0 | 0 |
| 0.5 | −5.2 | ND[b] | ND | ND | ND |
| 1.0 | 9.8 | ND | ND | ND | ND |
| 2.0 | 17.0 | ND | ND | ND | ND |
| 5.0 | 13.7 | 50.2 | 43.1 | −7.3 | 89.4 |
| 10 | 11.4 | 60.9 | 20.5 | 5.2 | 87.6 |
| 20 | ND | 34.1 | 0.8 | 44.2 | 88.9 |

[a]Peptide concentrations ranged from 1.5 to 10 × 10$^{-2}$ mM, whereas rPsaA concentrations ranged from 0.4 to 27.9 × 10$^{-4}$ mM.
[b]ND = not determined. The percent inhibitions given were the result of four separate experiments performed in duplicate by 3 different operators.

Serum Inhibition of Adherence

Percent inhibitions of adherence (% IA) were determined for nine sera from normal healthy adults to evaluate the functional antibodies to each of the peptides and to rPsaA protein. Adherence inhibition of target fluospheres to the Detroit 562 cells was observed, if a serum sample contained functional antibodies. Percent inhibitions of adherence at a 1:8 serum dilution for these nine sera are given in Table 10. Since these sera were from normal adult donors, determination of conventional titers as the dilution with at least 50% inhibition of adherence of PsaA-coated fluospheres yielded very similar titers for most sera (titer range=8 to 32) with the exception of serum 7083 (titer=128). Serum 7051 was adsorbed to remove the anti-PsaA antibodies. For all sera, % IA was similar when either rPsaA-, P1-, or P4-coated fluospheres were used in the adherence assays. Inhibition of adherence for rPsaA-coated fluospheres highly correlated with the inhibitions observed for P1- and P4-coated fluospheres (r≧0.794, P<0.05). No significant correlations (r≦0.318, P>0.10) were observed for P2- and P3-coated fluospheres when compared to rPsaA-coated fluospheres. These results indicate that the P1 peptide contains both immunoreactive and functional epitopes for rPsaA. Peptide P1 was localized to the region between amino acid 251 and 278 (P4 peptide sequence) of the rPsaA pneumococcal protein.

TABLE 10

Percent inhibition of adherence of rPsaA- or peptide coated fluospheres by adult human sera.

| Serum | IgG[a] | PsaA-coated | P1-coated | P2-coated | P3-coated | P4-coated |
|---|---|---|---|---|---|---|
| 7005[b] | 3.5 | 86.6 | 85.8 | 28.1 | 24.7 | 80.5 |
| 7051 | 19.4 | 97.0 | 69.7 | 22.6 | 7.1 | 56.0 |
| 7055 | 3.6 | 65.2 | 61.2 | 28.0 | 13.4 | 75.0 |
| 7059 | 2.2 | 63.7 | 46.5 | 55.6 | 22.5 | 63.5 |
| 7060 | 14.6 | 68.7 | 64.1 | 53.0 | 41.1 | 72.0 |
| 7072 | 3.0 | 80.3 | 75.7 | 28.2 | 24.7 | 66.0 |
| 7074 | 17.7 | 79.3 | 59.8 | 61.1 | 31.5 | 74.0 |
| 7083 | 565.2 | 89.6 | 72.0 | 31.7 | 24.1 | 86.0 |
| 7164 | ND[c] | 86.0 | 76.3 | 59.0 | 16.2 | 89.0 |

Figure 8:
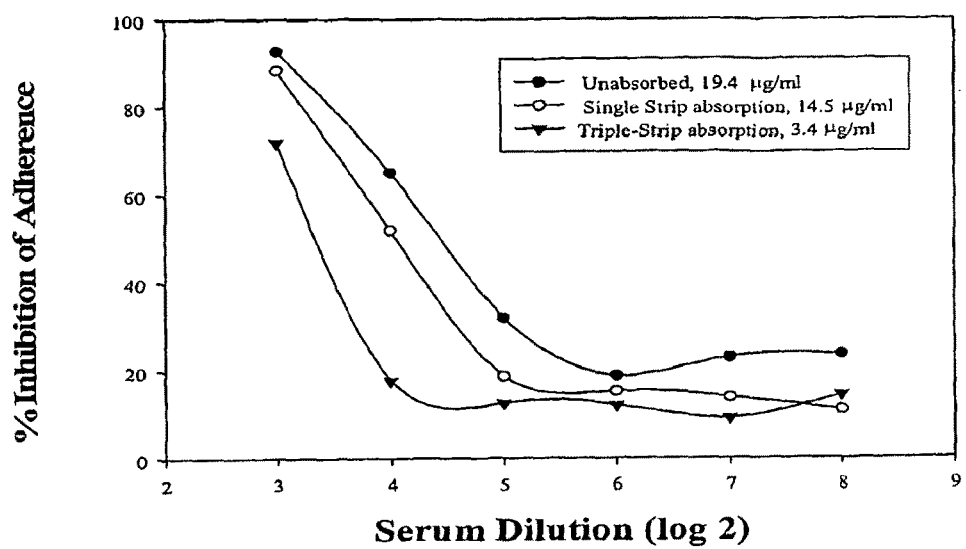
FIG. 8 shows the effect of partial adsorption of PsaA antibodies in serum 7051 in the inhibition of adherence of rPsaA-coated fluorospheres.

[a]Anti-PsaA IgG antibody concentration (μg/ml) as measured by ELISA.
[b]Each adult donor serum was diluted 2-fold for a total of 6 dilutions. The percent inhibition of adherence given is for the 1:8 serum dilution. The percent of inhibition of adherence given is the average of at least two separate experiments performed in duplicate.
[c]ND = not determined Effect of Partial Adsorption of Anti-PsaA Antibodies Serum 7051 was adsorbed with 3 nitrocellulose strips (2 hours, at room temperature) saturated with PsaA protein to remove PsaA antibodies (FIG. 8). However, after 3 sequential adsorptions only partial removal of PsaA antibodies was accomplished (initial anti-PsaA IgG antibody concentration 19.4 μg/ml, after one strip adsorption=14.5 μg/ml and after 3 strip-absorption=3.4 μg/ml). When the adsorbed 7051 serum was diluted 1:16, the inhibition of adherence of PsaA-coated fluospheres was reversed by 72%. Adsorbed serum 7051 (1:16 dilution) inhibited the adherence of rPsaA-, P1-, P2-, P3-coated fluospheres by 59.2, 54.4, −6.9, and 10.8%, respectively. We only monitored the decrease in IgG concentration. It is possible, that the presence of other antibody classes (especially IgA) may have an important role in preventing the binding of PsaA at the mucosal level.

PsaA is a common protein vaccine candidate currently under evaluation for use in combination with other pneumococcal proteins. Development of specific and reproducible in vitro assays for the measurement of functional antibodies to PsaA is needed. Although pneumococci have multiple adhesins, in this study we have shown that PsaA is a pneumococcal adhesin that specifically binds to human NP cells. In this study, PsaA-coated fluospheres showed high binding capacity to Detroit 562 cells (FIGS. 5 and 6). Measurement of antibodies capable of inhibiting the adherence of a single adhesin (PsaA) or related peptides reduces the potential for inhibition of adherence by antibodies to other adhesins, as reported previously when the live pneumococci are used in these assays (Romero-Steiner). Also, adherence of live pneumococci is dependent on the opacity phenotype of the Pnc strain (Anderson, Weisser). Therefore, higher throughput and specificity are needed in assays that evaluate the functional antibodies to rPsaA in future large scale immunogenicity studies. Fluosphere coating was quite reproducible from batch to batch and shelf life was approximately 3 months at 4° C. protected from light.

In this study, peptides P1 and P4 inhibited most of the adherence of PsaA-coated fluospheres, which indicates that these peptides contain a functional epitope(s) for PsaA adherence to nasopharyngeal cells (FIG. 4). The P1 sequence identified by analysis of the phage display library is not very similar to the PsaA sequence and it has the potential of alignment to six different regions in the PsaA sequence. Our adherence studies with the complete rPsaA and its peptides allowed for a better localization of the P1 sequence and the identification of the P4 peptide sequence.

Competitive inhibitions of rPsaA-coated fluospheres with P3 peptide were quite variable. However, when unsaturated fluospheres were used (530 μg/ml of rPsaA), the P3 peptide could enhance the binding of rPsaA fluospheres (<2.5-fold, data not shown). This type of bimodal interaction is currently under investigation and it may indicate the possibility of an inducible receptor in the nasopharyngeal cell that is dependent upon the concentration of rPsaA. In this study, we also show that the overall adherence of PsaA is dependent upon the concentration of rPsaA used to generate coated fluospheres (FIG. 6).

An interesting finding was the high adherence of P1-coated fluospheres, which adhered better to the Detroit 562 cells than rPsaA-coated fluospheres. These results could be explained in terms of the relative higher number of binding epitope(s) on the surface of the P1-coated fluospheres as compared to the rPsaA-coated fluospheres. Adherence of PsaA-coated fluospheres was better inhibited by addition of its related peptides than the purified protein in solution. Cold chase experiments with non-fluorescent spheres coated with PsaA protein showed higher percentages of inhibition (up to 31%) of the adherence PsaA-coated fluospheres. These results suggest that the PsaA protein has very high affinity for a receptor(s) in NP cells. It is possible that a conformational epitope(s) is needed for blocking the adherence of the whole protein. This indicates the presence of a conformational binding epitope(s) for the PsaA lipoprotein acting as an adhesin in vivo. The P1, P2 and P3 peptides used in this investigation were derived from a phage display library and have low amino acid sequence identity with the rPsaA (Srivastrava). However their functional capacity to protect mice against nasopharyngeal carriage of pneumococci has been previously reported (Johnson). Evaluation of the functional antibodies in adult human sera showed that antibodies to P1 and P4 (homologous peptide) are more prevalent, since these peptides had higher percentages of inhibition of adherence than the P2 and P3 peptides. Not all sera had similar capacity to inhibit the binding of the various peptide-coated fluospheres. This heterogeneity in the antibody populations of normal adults indicates the potential identification of relevant epitopes of PsaA and other pneumococcal adhesins using this type of approach. It also has potential for development of highly needed diagnostic assays to monitor non-invasive pneumococcal disease (Scott).

In summary, these results indicate that peptides P1 and P4 contain functional epitope(s) of PsaA that mediate adhesion to nasopharyngeal epithelial cells. The use of rPsaA, P1 or P4 peptides to coat fluospheres can be used for adherence inhibition assays. Major advantages of this assay format are the detection of fluorescent units using a fluorometer with high signal to noise ratios, as well as, faster data collection than determination of colony forming units which require overnight incubation of the assay plates. This type of adherence assay should be further evaluated by using pre and post-vaccination sera in immunogenicity studies of this vaccine candidate. An additional application is the use of specific peptides in the diagnosis of pneumococcal disease. Specific peptides are less likely to react with cross-reactive antibodies elicited by related microorganisms found in the normal flora of the nasopharynx. Further evaluation of anti-PsaA antibodies generated in response to Pnc colonization and acute otitis media is ongoing. The present assay can be used to establish correlates of protection needed in the evaluation of this type of pneumococcal vaccine.

Example 5

P4 Activates Professional and Non-Profession Phagocytes

P4 Activation Protocol:

Cell suspensions of HL-60 (promyelocytes) and RAW 264.7 (monocytes), and Detroit 562 cells (nasopharyngeal epithelial cells) were centrifuged at 1000 rpm-10 min and the pellet was resuspended in 1 ml PBS buffer. To this, P4 solution (1 mg/ml) was added at 10% (v/v) concentration, mixed by inverting few times and incubated at 37° C., 5% CO2 for 15 min (HL-60 and RAW) or 30 min (Detroit 562). After incubation, the cells were centrifuged again and the supernatant was analyzed for cytokines and the cell pellet was washed once in PBS, fixed in 2% glutaraldehyde and processed for transmission electron microscopic (TEM) analysis. Changes in cytokine release were recorded in treated cells wherein certain cytokine release/production such as EGF, IL8 were down regulated, and FGFbasic was up regulated. TEM and light photomicrographs demonstrate phagocytic activation in treated cells with characteristic membranous extension, foamy and granular cytoplasm, and vacuoles.

Example 6

Dual Peptide Function

Apart from immunogenicity, P4 peptide has 2 other biological activities; 1) adherence to nasopharyngeal (NP) epithelial cell and 2) activation of cells with special reference to professional and non-professional (phagocytic) cells. Adherence of P4 peptide to NP cells was demonstrated with P4 peptide coated fluorescent beads with the in vitro adherence assay using Detroit 562 cells. Dose dependant cellular activation property in P4 peptide was demonstrated with direct exposure of different cell lines such as Detroit 562 NP cells, HL-60 (phagocytes), and RAW 24.5 (monocytes) to P4 solution (example 5). Transmission electron micrographs and enhancement in bacterial adherence to P4 treated NP cells demonstrate this effect clearly.

With 2 major cellular activities in a single peptide, the protein sequence of P4 was analyzed with NCBI BLAST search engine. The carboxyl terminal sequences—QDTNIPIYAQI (SEQ ID NO:16)—had sequence homology (E value: >10) with transcriptional regulator protein of *Lactobacillus gasseri*, *Streptococcus* sp., *Enterococcus faecalis*, and *Bacillus licheniformis*. The property of activation and adherence can be separated with the segment of peptide at carboxyl terminal imparting the activation property and the remaining segment for adherence. Based on this P6, 11 amino acid peptide with the sequence—QDTNIPIYAQI (SEQ ID NO:16) and P7 the remaining part of P4 sequence, LFVESSVKRRPMKTVS (SEQ ID NO:17) were synthesized and analyzed for activation and/or adherence to NP cells singly or together.

Example 7

P4-Stimulated Cells Express FGFbasic and Enhance Fibroblast Growth 2 fibroblast cell lines, LEC-5 and NEO, were used. These cells were grown in a 96 well titer plates until they become confluent (~6 days). To this, the P4 treated cell supernatant that had higher concentration of FGFbasic was added at different concentrations and the growth was monitored fluorometrically with the help of a fluorometric metabolic indicator. An enhancement in the growth for fibroblasts with the treatment composition (supernatant) was observed.

REFERENCES

1. Anderson, B., J. Dahmen, F. Torbjörn, H. Leffler, G. Magnusson, G. Noori, and C. Svanborg Eden. 1983. Identification of an active disaccharide unit of a glycoconjugate receptor for pneumococci attaching to human pharyngeal epithelial cells. J. Exp. Med. 158:559-570.
2. Anderson, B., B. Eriksson, E. Falsen, A. Fogh, L. Å. Hanson, O, Nylén, H. Peterson, and C. Svanborg Eden. 1981. Adhesion of *Streptococcus pneumoniae* to human pharyngeal epithelial cells in vitro: differences in adhesive capacity among strains isolated from subjects with otitis media, septicemia, or meningitis or from healthy carriers. Infect. Immun. 32:311-317.
3. Berry, A. M. and J. C. Paton. 1996. Sequence heterogeneity of PsaA, a 37-kilodalton putative adhesin essential for virulence of *Streptococcus pneumoniae*. Infect. Immun. 64:5255-5262.
4. Black, S., H. Shinefield, B. Fireman, E. Lewis, P. Ray, J. Hansen, L. Elvin, K. Ensor, J. Hackell, G. Siber, F. Malinoski, D. Madore, I. Chang, R. Kohberger, W. Watson, R. Austrian, K. Edwards, and the northern California Kaiser Permanente vaccine study center group. Efficacy, safety and immunogenicity of heptavalent pneumococcal conjugate vaccine in children. 2000. Pediatr. Infect. Dis. J. 19:187-195.
5. Briles, D. E., E. Ades, J. C. Paton, J. S. Sampson, G. M. Carlone, R. C. Huebner, A. Virolainen, E. Swiatlo, and S. K. Hollingshead. 2000. Intranasal immunization of mice with a mixture of the pneumococcal proteins PsaA and PspA is highly protective against nasopharyngeal carriage of *Streptococcus pneumoniae*. Infect. Immun. 68:796-800.
6. Centers for Disease Control and Prevention. 2000. Preventing pneumococcal disease among infants and young children: recommendations of the Advisory Committee on Immunization Practices (ACIP). MMWR 49 (No. RR-09): 1-38.
7. Coffey, T. J., M. C. Enright, M. Daniels, J. K Morona, R. Morona, W. Hryniewicz, J. C. Paton, and B. G. Spratt. 1998. Recombinatorial exchanges at the capsular polysaccharide biosynthetic locus lead to frequent serotype changes among natural isolates of *Streptococcus pneumoniae*. Mol. Microbiol. 27:73-83.
8. Cundell, D. R., J. N. Weiser, J. Shen, A. Young, and E. I. Tuomanen. 1995. Relationship between colonial morphology and adherence of *Streptococcus pneumoniae*. Infect. Immun. 63:757-761.
9. Dagan, R., R. Melamed, M. Muallem, L. Piglausky, D. Greengerg, O. Abramson, P. M. Mendelman, N. Bohidar, and P. Yagupsky. 1996. Reduction of nasopharyugeal carriage of pneumococci during the second year of life by a heptavalent conjugate pneumococcal vaccine. J. Infect. Dis. 174:1271-1278.
10. Dintilhac, A., G. Alloing, C. Granadel, and J-P, Clayerys. 1997. Competence and virulence of *Streptococcus pneumoniae*: Adc and PsaA mutants exhibit a requirement for Zn and Mn resulting from inactivation of putative ABC metal permeases. Mol. Microbiol. 25:727-739.
11. Johnson, S, Dykes, J K, Jue, D, Sampson, J S, Carlone, G M, Ades, E W. 2002. Inhibition of pneumococcal carriage in mice by subcutaneous immunization with peptides from the common surface protein Pneumococcal Surface Adhesin A. J. Infect. Dis. 185:489-96.

12. Johnston, J. W., L. E. Myers, M. M. Ochs, W. H. Benjamin, Jr., D. E. Briles, and S. K. Hollinsgbead. 2004. Lipoprotein PsaA in virulence of *Streptococcus pneumoniae*: surface accessibility and role in protection from superoxide. Infect. Immun. 72: 5858-5867.
13. Morrison, K. E., D. Lake, J. Crook, G. M. Carlone, E. Ades, R. Facklam, and J. S. Sampson. 2000. Confirmation of psaA in all 90 serotypes of *Streptococcus pneumoniae* by PCR and potential of this assay for identification and diagnosis. J. Clin. Microbiol. 38:434-437.
14. Obaro, S. K., R. A. Adegbola, W. A. S. Banya, B. M. Greenwood. 1996. Carriage of pneumococci after pneumococcal vaccination. Lancet 348:271-272.
15. Ogunniyi, A. D., R. L. Folland, D. E. Briles, S. K. Hollingshead, and J. C. Paton. 2000. Immunization of mice with combination of pneumococcal virulence proteins elicits enhanced protection against challenge with *Streptococcus pneumoniae*. Infect. Immun. 68:3028-3033.
16. Pelton, S. I. M. Figueira, R. Albut, and J. Reino. 2000. Natural history of experimental otitis media due to PspA, PsaA or CbpA deficient mutants, abstr. O38. In Program and Abstracts of the Second International Symposium on Pneumococci and Pneumococcal Diseases 2000. Smith-Kline Beecham Pharmaceuticals.
17. Rapola, S., V. Jantti, R. Haikala, R. Syrjanen, G. M. Carlone, J. S. Sampson, D. E. Briles, J. C. Paton, A. K Takala, T. M. Kilpi, and H. Käyhty. 2000. Natural development of antibodies to pneumococcal surface protein A, pneumococcal surface adhesin A, and pneumolysin in relation to pneumococcal carriage and acute otitis media. J. Infect. Dis. 182:1146-1152.
18. Romero-Steiner, S, Pilishvili, T, Sampson J, Johnson S, Stinson, A, Carlone, G, Ades E. 2001. Inhibition of Pneumococcal Adherence to Human Nasopharyngeal Epithelial Cells by Anti-Psa Antibodies. Clin. Diagn. Lab. Immunology. 10:246-251.
19. Sampson, J. S., S. P. O'Connor, A. R. Stinson, J. A. Tharpe, and H. Russell. 1994. Cloning and nucleotide sequence analysis of psaA, the *Streptococcus pneumoniae* gene encoding a 37-kilodalton protein homologous to previously reported *Streptococcus* sp. adhesins. Infect. Immun. 62:319-324.
20. Seo, J-Y., S. Y. Seong, B-Y. Ahn, I. C. Kwon, H. Chung, and S. Y. Jeong. 2002. Cross-protective immunity of mice induced by oral immunization with pneumococcal surface adhesin A encapsulated in microspheres. Infect. Immun. 70:1143-1149.
21. Srivastrava, N., J. L. Zeiler, S. L. Smithson, et al. 2000. Selection of an immunogenic and protective epitope of the PsaA protein of *Streptococcus pneumoniae* using phage display library. Hybridoma. 19:23-31.
21. Tharpe, J. A., H. Russell, M. Leinonen, B. D. Plikaytis, R. F. Breiman, G. M. Carlone, E. W. Ades, and J. S. Sampson. 1998. Comparison of a pneumococcal common protein (PsaA) antibody ELISA and a PsaA immune complex ELISA for detection of pneumococcal serum antibody. Pathobiology. 66:77-83.
22. Weiser, J. N., E. I. Tuomanen, D. R. Cundell, P. K. Sreenivasan, R. Austrian, and H. R. Masure. 1994. The effect of colony opacity variation on pneumococcal colonization and adhesion. J. Cell. Biochem. 18A:S55.
23. Weiser, J. N., Z. Markiewicz, E. I. Tuomanen, and J. H. Wani. 1996. Relationship between phase variation in colony morphology, intrastrain variation in cell wall physiology, and nasopharyngeal colonization by *Streptococcus pneumoniae*. Infect. Immun. 64:2240-2245.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What we claim is:

1. An isolated peptide comprising the amino acid sequence of SEQ ID NO: 1.

2. An isolated peptide comprising the amino acid sequence of SEQ ID NO: 2.

3. A method of inhibiting binding of pneumococcal surface adhesin protein A (PsaA) to cells that express a PsaA receptor, comprising contacting the cell with the isolated peptide of claim 1.

4. A method of inhibiting binding of pneumococcal surface adhesin protein A (PsaA) to cells that express a PsaA receptor, comprising contacting the cell with the isolated peptide of claim 2.

5. An immunogenic composition comprising the isolated peptide of claim 1 and a pharmaceutical carrier.

6. An immunogenic composition comprising the isolated peptide of claim 2 and a pharmaceutical carrier.

* * * * *

UNITED STATES PATENT AND TRADEMARK OFFICE
CERTIFICATE OF CORRECTION

| | | |
|---|---|---|
| PATENT NO. | : 7,919,104 B2 | Page 1 of 4 |
| APPLICATION NO. | : 11/992719 | |
| DATED | : April 5, 2011 | |
| INVENTOR(S) | : Ades et al. | |

It is certified that error appears in the above-identified patent and that said Letters Patent is hereby corrected as shown below:

<u>On the Title Page Item (56), under OTHER PUBLICATIONS</u>
"pneumonia" should read --*pneumoniae*--.

<u>In the Figures</u>
Figure 1, "0.53 µg ml" should read --0.53 µg/ml--.

Column 1, line 52, "fluospheres" should read --fluorospheres--.

Column 1, line 56, "Fluosphere" should read --fluorosphere--.

Column 2, line 2, "fluospheres" should read --fluorospheres--.

Column 2, line 5, "fluospheres" should read --fluorospheres--.

Column 3, line 44, "and in can" should read --and can--.

Column 3, line 58, "valiant" should read --variant--.

Column 4, Table 1, "allosoleucine" should read --alloisoleucine--.

Column 4, Table 1, "isolelucine" should read --isoleucine--.

Column 4, Table 1, "acidp" should read --acid--.

Column 5, Line 43, "6)" should read --5)--.

Column 6, line 24, "in, among other locations in," should read --in, among other locations,--.

Column 6, line 34, "stereo isomers" should read --stereoisomers--.

Column 6, line 35, "stereo isomers" should read --stereoisomers--.

Column 6, line 53, "CHH$_2$SC" should read --CHH$_2$SO--.

Column 7, line 3, "reference." should read --reference).--.

Column 7, line 34, "peptides.)" should read --peptides).--.

Signed and Sealed this
Twenty-second Day of May, 2012

David J. Kappos
*Director of the United States Patent and Trademark Office*

CERTIFICATE OF CORRECTION (continued)
U.S. Pat. No. 7,919,104 B2

Column 7, line 50, "three dimensional" should read --three-dimensional--.

Column 8, line 42, "F(ab')$_{21}$" should read --F(ab')$_2$,--.

Column 10, line 6, "referenced" should read --reference--.

Column 10, line 48, "heteromycloma" should read --heteromyeloma--.

Column 11, line 46, "2551-255" should read --2551-2555--.

Column 11, line 47, "2551-255" should read --2551-2555--.

Column 13, line 1, "acids" should read --acid--.

Column 13, line 16, "(1982)." should read --(1982)).--.

Column 13, line 50, "(Fe)" should read --(Fc)--.

Column 15, line 27, "peptides or polypeptides are" should read --peptide or polypeptide is--.

Column 15, line 41, "from to 2 μg" should read --from 2 μg--.

Column 15, line 42, "and" should read --an--.

Column 16, line 41, "lozenges oral" should read --lozenges, oral--.

Column 17, line 28, "biding" should read --binding--.

Column 17, line 33, "mimic" should read --mimetic--.

Column 17, line 36, "mimic" should read --mimetic--.

Column 17, line 41, "mimic" should read --mimetic--.

Column 17, line 60, "mimic" should read --mimetic--.

Column 18, line 33, "to by" should read --to be--.

Column 18, line 55, "and," should read --and--.

Column 19, line 52, "(i.e. are" should read --(i.e. a--.

Column 20, line 64-65, "bacteria, including" should read --bacteria (including--.

Column 21, line 7, "cells is disclosed." should read --cells.--.

Column 23, line 13, "peptide See" should read --peptide. See--.

Column 23, line 32, "any means" should read --includes any means--.

Column 23, line 38, "but not" should read --but are not--.

Column 23, line 64, "base" should read --based--.

Column 24, line 29, "CHARm" should read --CHARMm--.

Column 24, line 41, "Toxiciol." should read --Toxicol.--.

Column 24, line 52, "design of" should read --design--.

Column 24, line 58, "mimic" should read --mimetic--.

Column 25, line 15-16, "12997-302" should read --12297-12302--.

Column 25, line 45, "12997-302" should read --12297-12302--.

CERTIFICATE OF CORRECTION (continued)
U.S. Pat. No. 7,919,104 B2

Column 26, line 30, "6,025,371)" should read --6,025,371),--.

Column 26, line 33, "719)" should read --719),--.

Column 26, line 42, "107)" should read --107),--.

Column 26, line 46, "U.S." should read --(U.S.--.

Column 29, line 25, "VRR" should read --VKRR--.

Column 29, line 27, "RPV" should read --RPMKTV--.

Column 29, line 44, "RKTV" should read --RPMKTV--.

Column 30, line 52, "V-H-H-R-P" should read --V-H-R-R-P--.

Column 31, line 28, "100 μg" should read --10 μg--.

Column 33, line 51, "bleed" should read --bleed*--.

Column 34, line 61-62, "Srivastrava" should read --Srivastava--.

Column 35, line 10, "K-R" should read --K–R--.

Column 35, line 44, "over night" should read --overnight--.

Column 35, line 47, "a-30-minute" should read --a 30-minute--.

Column 36, line 67, "401" should read --40 μl--.

Column 37, line 14, "adherence The" should read --adherence. The--.

Column 37, line 50, "a-140" should read --a 140--.

Column 39, line 26, "19.4" should read --= 19.4--.

Column 39, line 27, "absorption" should read --adsorption--.

Column 40, line 31, "Srivastrava" should read --Srivastava--.

Column 41, line 3, "Non-Profession" should read --Non-Professional--.

Column 41, line 12, "inverting few times" should read --inverting a few times--.

Column 41, line 12, "CO2" should read --$CO_2$--.

Column 41, line 31, "cell" should read --cells--.

Column 41, line 35, "dependant" should read --dependent--.

Column 41, line 64, "a 96 well titer plates" should read --a 96 well titer plate--.

Column 41, line 64, "become" should read --became--.

Column 41, line 67 to Column 42, line 1, "fluormetrically" should read --fluorometrically--.

Column 42, line 13, "O," should read --O.--.

Column 42, line 53, "Greengerg" should read --Greenberg--.

Column 42, line 54, "nasopharyugeal" should read --nasopharyngeal--.

Column 42, line 58, "J-P," should read --J.-P.--.

Column 42, line 58, "Clayerys" should read --Claverys--.

CERTIFICATE OF CORRECTION (continued)
U.S. Pat. No. 7,919,104 B2

Column 43, line 2, "Hollinsgbead" should read --Hollingshead--.

Column 43, line 20, "S. I. M." should read --S. I., M.--.

Column 44, line 12, "Srivastrava" should read --Srivastava--.

Column 44, line 15, "21" should read --22--.

Column 44, line 21, "22" should read --23--.

Column 44, line 25, "23" should read --24--.

SEQUENCE LISTING

```
<160> NUMBER OF SEQ ID NOS: 18

<210> SEQ ID NO 1
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 1

Leu Phe Val Glu Ser Ser Val Lys Arg Arg Pro Met Lys Thr Val Ser
1               5                   10                  15

Gln Asp Thr Asn Ile Pro Ile Tyr Ala Gln Ile Phe
            20                  25

<210> SEQ ID NO 2
<211> LENGTH: 36
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 2
```

-continued

```
Val Pro Ser Leu Phe Val Asp Ser Ser Val Asp Asp Arg Pro Met Lys
1               5                   10                  15

Thr Val Ser Gln Asp Thr Asn Ile Pro Ile Tyr Ala Gln Ile Phe Thr
            20                  25                  30

Asp Ser Ile Ala
        35

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 3

Thr Val Ser Arg Val Pro Trp Thr Ala Trp Ala Phe His Gly Tyr
1               5                   10                  15

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 4

Arg Ser Tyr Gln His Asp Leu Arg Ala Tyr Gly Phe Trp Arg Leu
1               5                   10                  15

<210> SEQ ID NO 5
<211> LENGTH: 15
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 5

Leu Val Arg Arg Phe Val His Arg Arg Pro His Val Glu Ser Gln
1               5                   10                  15

<210> SEQ ID NO 6
<211> LENGTH: 34
<212> TYPE: PRT
<213> ORGANISM: Artificial Sequence
<220> FEATURE:
<223> OTHER INFORMATION: Description of Artificial Sequence;
      note=synthetic construct
<220> FEATURE:
<221> NAME/KEY: MISC_FEATURE
<222> LOCATION: (1)..(1)
<223> OTHER INFORMATION: Xaa can be = His, Val, Ile or Leu
<220> FEATURE:
<221> NAME/KEY: MISC_FEATURE
<222> LOCATION: (2)..(2)
<223> OTHER INFORMATION: Xaa can be His, Pro or Gly
<220> FEATURE:
<221> NAME/KEY: MISC_FEATURE
<222> LOCATION: (3)..(3)
<223> OTHER INFORMATION: Xaa can be His, Ser or Thr
<220> FEATURE:
<221> NAME/KEY: MISC_FEATURE
<222> LOCATION: (32)..(32)
<223> OTHER INFORMATION: Xaa can be His, Thr or Ser
<220> FEATURE:
<221> NAME/KEY: MISC_FEATURE
<222> LOCATION: (33)..(33)
<223> OTHER INFORMATION: Xaa can be His or Asp
<220> FEATURE:
```

```
<221> NAME/KEY: MISC_FEATURE
<222> LOCATION: (34)..(34)
<223> OTHER INFORMATION: Xaa can be His, Ser or Thr

<400> SEQUENCE: 6

Xaa Xaa Xaa Leu Phe Val Glu Ser Ser Val Lys Arg Arg Pro Met Lys
1               5                   10                  15

Thr Val Ser Gln Asp Thr Asn Ile Pro Ile Tyr Ala Gln Ile Phe Xaa
            20                  25                  30

Xaa Xaa

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 7

Leu Phe Val Glu Ser Ser Val Asp Asp Arg Pro Met Lys Thr Val Ser
1               5                   10                  15

Lys Asp Thr Asn Ile Pro Ile Tyr Ala Lys Ile Phe
            20                  25

<210> SEQ ID NO 8
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 8

Leu Phe Val Glu Ser Ser Val Asp Asp Arg Pro Met Lys Thr Val Ser
1               5                   10                  15

Lys Asp Thr Asn Ile Pro Ile Tyr Ser Thr Ile Phe
            20                  25

<210> SEQ ID NO 9
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 9

Leu Phe Val Glu Ser Ser Val Asp Asp Arg Pro Met Lys Thr Val Ser
1               5                   10                  15

Lys Asp Thr Asn Ile Pro Ile His Ala Lys Ile Phe
            20                  25

<210> SEQ ID NO 10
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 10

Leu Phe Val Glu Ser Ser Val Asp Asp Arg Pro Met Glu Thr Val Ser
1               5                   10                  15

Lys Asp Ser Gly Ile Pro Ile Tyr Ala Glu Ile Phe
```

```
<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 11

Leu Phe Val Glu Ser Ser Val Asp Arg Arg Pro Met Glu Thr Val Ser
1               5                   10                  15

Lys Asp Ser Gly Ile Pro Ile Tyr Ser Glu Ile Phe
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 12

Leu Phe Val Glu Ser Ser Val Asp Lys Arg Pro Met Lys Ser Val Ser
1               5                   10                  15

Arg Glu Ser Gly Ile Pro Ile Tyr Ala Glu Ile Phe
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 13

Leu Phe Val Glu Ser Ser Val Asp Asp Arg Pro Met Lys Thr Ile Ser
1               5                   10                  15

Lys Glu Thr Gly Ile Ser Ile Tyr Ser Lys Ile Phe
            20                  25

<210> SEQ ID NO 14
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 14

Leu Phe Val Glu Thr Ser Val Asp Arg Arg Ser Met Glu Thr Val Ser
1               5                   10                  15

Lys Glu Thr Asn Val Pro Ile Ala Gly Thr Ile Phe
            20                  25

<210> SEQ ID NO 15
<211> LENGTH: 28
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 15
```

```
Leu Phe Val Glu Thr Ser Val Asp Pro Arg Ser Met Glu Ser Val Ser
1               5                   10                  15

Lys Glu Thr Gly Val Pro Ile Phe Ala Lys Ile Phe
                20                  25
```

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 16

```
Gln Asp Thr Asn Ile Pro Ile Tyr Ala Gln Ile
1               5                   10
```

<210> SEQ ID NO 17
<211> LENGTH: 16
<212> TYPE: PRT
<213> ORGANISM: Artificial Sequence
<220> FEATURE:
<223> OTHER INFORMATION: Description of Artificial Sequence;
      note=synthetic construct

<400> SEQUENCE: 17

```
Leu Phe Val Glu Ser Ser Val Lys Arg Arg Pro Met Lys Thr Val Ser
1               5                   10                  15
```

<210> SEQ ID NO 18
<211> LENGTH: 30
<212> TYPE: PRT
<213> ORGANISM: Artificial Sequence
<220> FEATURE:
<223> OTHER INFORMATION: Portion of PsaA protein

<400> SEQUENCE: 18

```
Asp Ser Ile Ala Glu Gln Gly Lys Glu Gly Asp Arg Tyr Tyr Ser Met
1               5                   10                  15

Met Lys Tyr Asn Leu Asp Lys Ile Ala Glu Gly Leu Ala Lys
                20                  25                  30
```